(12) United States Patent
Pratt

(10) Patent No.: US 11,686,714 B2
(45) Date of Patent: *Jun. 27, 2023

(54) DEVICE AND METHOD FOR DETECTING RESTRICTIONS IN GAS ACCESS TO A GAS SENSOR

(71) Applicant: HONEYWELL INTERNATIONAL INC., Charlotte, NC (US)

(72) Inventor: Keith Francis Edwin Pratt, Hampshire (GB)

(73) Assignee: HONEYWELL INTERNATIONAL INC., Charlotte, NC (US)

(*) Notice: Subject to any disclaimer, the term of this patent is extended or adjusted under 35 U.S.C. 154(b) by 191 days.

This patent is subject to a terminal disclaimer.

(21) Appl. No.: 17/128,379

(22) Filed: Dec. 21, 2020

(65) Prior Publication Data

US 2021/0148874 A1 May 20, 2021

Related U.S. Application Data

(63) Continuation of application No. 16/160,454, filed on Oct. 15, 2018, now Pat. No. 10,900,942.

(51) Int. Cl.
*G01N 33/00* (2006.01)
*G01N 27/407* (2006.01)
*G01N 27/31* (2006.01)

(52) U.S. Cl.
CPC .......... *G01N 33/007* (2013.01); *G01N 27/31* (2013.01); *G01N 27/4078* (2013.01); *G01N 33/0062* (2013.01); *G01N 33/004* (2013.01); *G01N 2033/0068* (2013.01); *G01N 2033/0072* (2013.01)

(58) Field of Classification Search
CPC .. G01N 27/4078; G01N 27/31; G01N 33/007; G01N 2033/0072
See application file for complete search history.

(56) References Cited

U.S. PATENT DOCUMENTS 6,358,384 B1 3/2002 Warburton et al.
6,558,519 B1 5/2003 Dodgson et al.
(Continued)

FOREIGN PATENT DOCUMENTS

CN 1244258 A 2/2000
CN 101339157 A 1/2009
(Continued)

OTHER PUBLICATIONS

Communication Pursuant to Article 94(3) issued in European Application No. 19203117.7 dated Jul. 14, 2021, 3 pages.
(Continued)

*Primary Examiner* — Paul M. West
(74) *Attorney, Agent, or Firm* — Alston & Bird LLP

(57) ABSTRACT

Provided is a gas sensor and methods of monitoring the same. The gas sensor may detect gas restrictions within the gas sensor. The gas sensor may include a test gas diffusion path allowing for monitoring of restrictions within the gas sensor. A pulse of test gas may be electrochemically generated into a void disposed between the membrane and capillary of the gas sensor. The resulting transient signal on the sensing electrode may be analyzed to determine the degree of restriction present in the gas sensor.

20 Claims, 14 Drawing Sheets

(56) References Cited

U.S. PATENT DOCUMENTS

| | | | |
|---|---|---|---|
| 6,632,674 | B1 | 10/2003 | Warburton |
| 6,635,160 | B1 | 10/2003 | Dodgson |
| 6,948,352 | B2 | 9/2005 | Rabbett et al. |
| 9,012,345 | B2 | 4/2015 | Masel et al. |
| 9,555,367 | B2 | 1/2017 | Masel et al. |
| 10,900,942 | B2 * | 1/2021 | Pratt .................... G01N 33/007 |
| 2005/0100478 | A1 | 5/2005 | Harvey |
| 2006/0283707 | A1 | 12/2006 | Kuhn |
| 2008/0041730 | A1 | 2/2008 | Caro et al. |
| 2013/0075273 | A1 | 3/2013 | Masel et al. |
| 2013/0087457 | A1 | 4/2013 | Pratt et al. |
| 2017/0269044 | A1 | 9/2017 | Diekmann |

FOREIGN PATENT DOCUMENTS

| | | |
|---|---|---|
| CN | 102914575 A | 2/2013 |
| CN | 105980843 A | 9/2016 |
| CN | 108351319 A | 7/2018 |
| EP | 2581735 A1 | 4/2013 |

OTHER PUBLICATIONS

CN Office Action dated Jan. 17, 2022, including Search Report, for CN Application No. 201910968712, 8 pages.

English Translation of CN Office Action dated Jan. 17, 2022, including Serach Report, for CN Application No. 201910968712, 11 pages.

U.S. Appl. No. 16/160,454, filed Oct. 14, 2018, U.S. Pat. No. 10,900,942, Patented.

Chen et al., Mechanism of CO Formation in Reverse Water-Gas Shift Reaction Over Cu/A12O2 Catalyst, Jun. 8, 2000, Catalysis Letters 68; pp. 45-48, https://rd.springer.com/article/10.1023/A:1019071117449.

Extended European Search Report for Application No. 19203117.7, dated Mar. 4, 2020, 8 pages.

Kumar et al., Controlling the Product Syngas H2:CO Ratio Through Pulsed-Bias Electrochemical Reduction f CO2 on Copper, Jun. 8, 2016, ACS Catalysis, pp. 4739-4745, http://pubs.acs.org/doi/abs/10.1021/acscatal.6b00857, Jan. 9, 2019.

Masel et al., CO2 Conversion to Chemicals with Emphasis on Using Renewable Energy/Resources to Drive the Conversion, Nov. 19, 2015, Commercializing Biobased Products: Opportunities, Challenges, Benefits, and Risks, Chapter 10, pp. 215-257, https://books.google.fr/books?hl=en&lr=&id=WW72CgAAQBAJ&oi-fnd&pg=PA215&dq=electrochemical+%22carbon+monoxide+generator% .

Non-Final Rejection dated Jun. 16, 2020 for U.S. Appl. No. 16/160,454.

Notice of Allowance and Fees Due (PTOL-85) dated Sep. 22, 2020 for U.S. Appl. No. 16/160,454.

Observations by third parties Mailed on May 6, 2020 for EP Application No. 19203117.7.

Wenzel et al., CO Production From CO2 via Reverse Water-Gas Shift Reaction Performed in a Chemical Looping Mode: Kinetics on Modified Iron Oxide, Nov. 28, 2016, Journal of CO2 Utilization, pp. 60-68, http://www.sciencedirect.com/science/article/pii/S2212982016300439?via%3Dihub, Jan. 9, 2019.

CN Notice of Allowance dated Jun. 8, 2022 for CN Application No. 201910968712, 2 pages.

English translation of CN Notice of Allowance dated Jun. 8, 2022 for CN Application No. 201910968712, 3 pages.

EP Office Action dated Feb. 14, 2023 for EP Application No. 19203117, including Annex.

\* cited by examiner

DEVICE AND METHOD FOR DETECTING RESTRICTIONS IN GAS ACCESS TO A GAS SENSOR

CROSS-REFERENCE TO RELATED APPLICATIONS

This application is a continuation of U.S. patent application Ser. No. 16/160,454, filed Oct. 15, 2018, which is hereby incorporated herein by reference in its entirety.

BACKGROUND

Gas sensors are commonly used to detect the presence of various target gases, such as carbon monoxide. Applicant has identified a number of deficiencies and problems associated with conventional gas sensors. Through applied effort, ingenuity, and innovation, many of these identified problems have been solved by developing solutions that are included in embodiments of the present invention, many examples of which are described in detail herein.

BRIEF SUMMARY

In general, embodiments of the present invention provided herein include methods, devices, systems, and computer program products for detecting gas restrictions in gas sensors. In some embodiments, a gas sensor is provided that includes a housing defining an opening to an external environment; a sensing electrode disposed in the housing and configured to generate a test gas signal when the sensing electrode is in contact with a test gas; a membrane disposed in the housing between the sensing electrode and the opening in the housing, where the membrane is at least partially exposed to the external environment; and a test gas diffusion path defined in the housing for the test gas to travel in the gas sensor and comprising an inlet and an outlet. The test gas diffusion path may be disposed between the membrane and the sensing electrode and may be configured such that when the test gas travels through the test gas diffusion path from the inlet to the outlet, the test gas comes in contact with the membrane prior to coming in contact with the sensing electrode and such that the test gas signal is higher when the membrane has a high degree of restriction compared to the test gas signal when the membrane has a low degree of restriction.

In some embodiments, the test gas diffusion path may include an inlet and an outlet, the inlet disposed distal to the sensing electrode and the outlet disposed proximal to the sensing electrode. In some embodiments, the test gas diffusion path may be configured such that when the test gas travels through the test gas diffusion path, the test gas comes in contact with the membrane prior to coming in contact with the sensing electrode and such that the test gas signal is higher when the membrane has a high degree of restriction compared to the test gas signal when the membrane has a low degree of restriction by comprising a first test gas diffusion path opening adjacent to the membrane and between the inlet and the outlet, wherein the sensing electrode is disposed at the outlet of the test gas diffusion path. In some embodiments, the first test gas diffusion path opening may be defined by a wall of the test gas diffusion path in the housing and may expose the test gas to the membrane. In some embodiments, the gas sensor may further include a test gas electrode configured to cause the test gas to be generated at the inlet of the test gas diffusion path.

In some embodiments, the test gas may include hydrogen, carbon monoxide, or combinations thereof. In some embodiments, the test gas may be generated electrochemically.

In some embodiments, the gas sensor may include a capillary disposed between the sensing electrode and the outlet of the test gas diffusion path. In some embodiments, the sensing electrode may be configured to cause a target gas signal to be generated when the sensing electrode is in contact with a target gas.

In some embodiments, the gas sensor may be configured to generate the test gas at periodic intervals of time.

In some embodiments, an integrated charge of the test gas signal may indicate the degree of restriction of the membrane. In some embodiments, the gas sensor further includes a capillary disposed between the sensing electrode and the outlet of the test gas diffusion path. A magnitude of the test gas signal may indicate a degree of restriction of the capillary. In some embodiments, the gas sensor may be configured to cause test gas to enter the inlet of the test gas diffusion path during a diagnostic mode and cause test gas to be restricted from entering the inlet of the test gas diffusion path during a normal operating mode.

In some embodiments, the gas sensor may be configured to switch from the diagnostic mode to the normal operating mode when the sensing electrode detects a target gas. In some embodiments, the inlet of the test gas diffusion path may be disposed concentrically around the sensing electrode. In some embodiments, the inlet of the test gas diffusion path may be disposed at a first end of the housing and the sensing electrode is disposed at a second end of the housing.

Another embodiment of the present invention provided is a gas sensor system including the gas sensor and an external test gas generator configured to generate test gas. When the external test gas generator generates test gas, the gas sensor and external test gas generator are operatively coupled such that test gas enters the inlet of the test gas diffusion path of the gas sensor.

Another embodiment of the present invention provided is a method of monitoring gas restriction in a gas sensor. The method may include causing a test gas to travel through a test gas diffusion path disposed in the gas sensor. The test gas diffusion path may include an inlet and an outlet. The test gas diffusion path may be disposed between a membrane and a sensing electrode and may be configured such that when the test gas travels through the test gas diffusion path from the inlet to the outlet, the test gas comes in contact with the membrane prior to coming in contact with the sensing electrode. The method may also include determining a degree of restriction in the gas sensor.

In some embodiments, determining the degree of restriction in the gas sensor may include receiving a test gas signal from the sensing electrode and integrating the test gas signal. The degree of restriction may be associated with the membrane.

In some embodiments, determining the degree of restriction in the gas sensor may include receiving a test gas signal from the sensing electrode and determining a peak current in the test gas signal. The degree of restriction may be associated with a capillary disposed between the membrane and the sensing electrode.

In some embodiments, the method may include generating a restriction compensation and applying such restriction compensation to a target gas signal in response to the degree of restriction.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE FIGURES

Reference will now be made to the accompanying drawings, which are not necessarily drawn to scale, and wherein.

DETAILED DESCRIPTION

Figure 1:
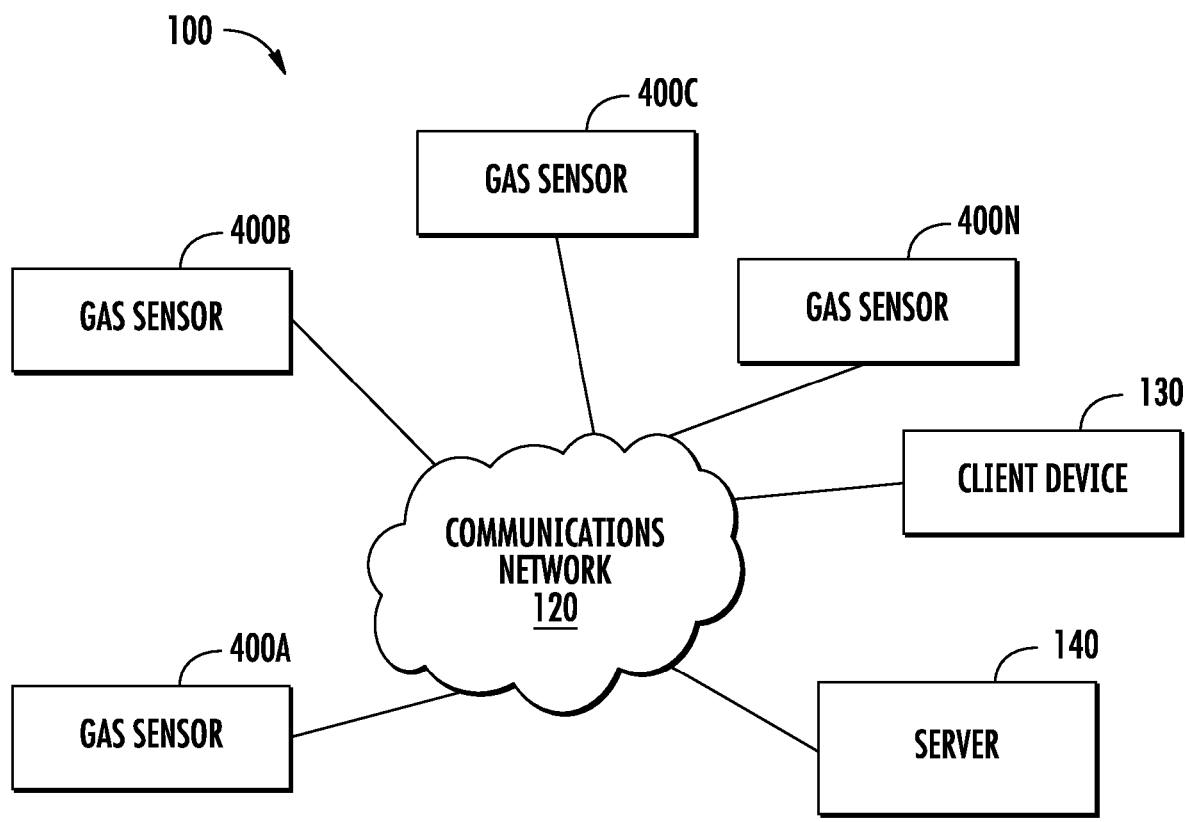
FIG. 1 illustrates an example system in accordance with some embodiments discussed herein.

Some embodiments of the present invention will now be described more fully hereinafter with reference to the accompanying drawings, in which some, but not all embodiments of the inventions are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

As used herein, the terms "data," "content," "digital content," "digital content object," "information," and similar terms may be used interchangeably to refer to data capable of being transmitted, received, and/or stored in accordance with embodiments of the present invention. Thus, use of any such terms should not be taken to limit the spirit and scope of embodiments of the present invention. Further, where a device is described herein to receive data from another device, it will be appreciated that the data may be received directly from the another device or may be received indirectly via one or more intermediary devices, such as, for example, one or more servers, relays, routers, network access points, base stations, hosts, repeaters, and/or the like, sometimes referred to herein as a "network." Similarly, where a device is described herein to send data to another device, it will be appreciated that the data may be sent directly to the another device or may be sent indirectly via one or more intermediary devices, such as, for example, one or more servers, relays, routers, network access points, base stations, hosts, repeaters, and/or the like.

The term "comprising" means including but not limited to, and should be interpreted in the manner it is typically used in the patent context. Use of broader terms such as comprises, includes, and having should be understood to provide support for narrower terms such as consisting of, consisting essentially of, and comprised substantially of.

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment).

The word "exemplary" is used herein to mean "serving as an example, instance, or illustration." Any implementation described herein as "exemplary" is not necessarily to be construed as preferred or advantageous over other implementations.

The terms "about" or "approximately" or the like, when used with a number, may mean that specific number, or alternatively, a range in proximity to the specific number, as understood by persons of skill in the art field.

If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

As used herein, the term "transmitter" refers to any component that can generate radio waves for communication purposes while a "receiver" is used to generally refer to any component that can receive radio waves and convert the information into useable form. A "transceiver" generally refers to a component that can both generate radio waves and receive radio waves and is thus contemplated when either a transmitter or a receiver is discussed.

Various embodiments of the disclosure are directed to systems, methods, and devices that are configured to detect the restriction of gas in a gas sensor. In particular, the systems, methods, and devices are configured to detect the restriction of gas access to the sensing electrode of the gas sensor. The restriction of gas access by a membrane or capillary of an electrochemical gas sensor may be detected, compensated for, and flagged for correction without the need to apply an external target gas and without the need for user intervention.

Prior gas sensors required bump testing where a pulse of the target gas is manually or automatically generated and applied to the gas sensor to test the ability of the gas sensor to identify the target gas. For instance, in some cases, an operator breathes on the gas sensor to test the operation of the gas sensor. In some cases, a pulse of target gas may be automatically generated using a bump test station, where an operator is required to physically move the gas sensor to the bump test station for testing. Fixed installations may include built in or piped in gas supply. However, such testing is inconvenient, costly, and potentially hazardous. In some applications, bump testing is required to be performed daily, thereby placing a significant burden on operators of the gas sensor. Other gas sensors may generate target gases externally or internally and then apply the target gas to the gas sensor to measure the performance of the gas sensor electrode. However, these gas sensors are not able to determine whether a blockage has been formed in the gas sensor, much less determine the degree of any blockage in the gas sensor.

Removal of the need to perform bump tests can save a significant amount of money over the lifetime of a gas sensor. Further, identification of partial or complete restriction or blockage of membranes and capillaries in gas sensors allows operators to identify failure modes and correct the failure modes prior to complete blockage (e.g., where partial restriction or blockage is identified). The ability to independently quantify the degree of restriction of the membrane and/or capillary may allow compensation to be applied and may allow the gas sensor to flag, in advance, the need to replace or clean a membrane or capillary. The need to replace the gas sensor itself can also be determined.

Provided herein is a self-contained and autonomous system, method, and device for detecting gas restrictions in gas sensors. The system, method, and device can be used to detect gas restrictions in gas sensors without significantly disturbing normal operations of the sensor.

In some embodiments, a pulse of test gas is electrochemically generated into a void ("test gas diffusion path") disposed between the membrane and sensing electrode of the gas sensor. The resulting transient signal on the sensing electrode is then analyzed. In some embodiments, the test gas is hydrogen, carbon monoxide, or any other suitable gas that can be applied to the gas sensor. The target gas can be various types of gases including oxygen as well as toxic gases such as carbon monoxide, sulphur dioxide, and hydrogen sulfide. The gas sensor may be a 2, 3, or more electrode (or other) amperometric design.

In some embodiments, a test gas is generated within the sensor housing (e.g., $H_2$, CO, etc. generated by a test gas electrode disposed within the gas sensor housing) and the resulting test gas signal on the sensing electrode may be used to determine the degree of restriction of the capillary and/or membranes. The test gas may be hydrogen produced by electrolysis of water in the electrolyte, or may be carbon monoxide produced electrochemically utilizing the reverse water gas shift reaction ($CO_2+H_2 \rightarrow CO+H_2O$) (CO2 is usually present and H2 can be generated electrochemically). The test gas may be fed into the test gas diffusion path between the capillary and the outer protective membrane. A portion of the test gas may reach the sensing electrode and may be detected, while a portion of the test gas may escape through the membrane of the gas sensor. A comparison of the total amount of test gas detected with the amount of test gas generated or applied to the gas sensor may provide a measure of the degree of restriction of the membrane. The magnitude of the test gas signal may provide a measure of the degree of capillary restriction.

The test gas may be generated as a pulse of known charge (e.g., a known number of moles of test gas generated). The integrated charge on the sensing electrode may measure the fraction of the test gas that has not escaped out of the gas sensor through the membrane. For example, a more restricted membrane may result in a greater fraction of the test gas being detected. To avoid overloading the gas sensor, the test gas pulse may be kept small and short, but sufficient to be detected by the sensing electrode and analyzed.

In some embodiments, the test gas pulse of known charge may be generated by a test gas electrode and fed into the test gas diffusion path between the membrane and the sensing electrode. A capillary may be present between the sensing electrode and the test gas diffusion path. A portion of the test gas may escape the gas sensor through the membrane. If the membrane is damaged or missing, then most of the test gas may escape the gas sensor. If the membrane is highly restricted or blocked, then very little test gas may escape the gas sensor leaving most of the test gas to be detected by the sensing electrode.

By having a test gas diffusion path between the membrane and the capillary (and thus between the membrane and the sensing electrode), the membrane may be considerably restricted before the sensing electrode sensitivity is affected. In some embodiments, the disclosed system, method, and device is able to detect restriction of the membrane long before the membrane becomes restricted enough to limit gas sensitivity, thereby providing an advanced warning of failure. In some embodiments, the system, method, and device enables compensation to be applied to the gas sensor to allow for increased restriction by membrane. In some embodiments, such as where the membrane is highly restricted, failure may be flagged. In some embodiments, the system, method, and device may also detect torn or missing membranes. For example, the amount of test gas that reaches the sensing electrode may be much lower than normal, indicating that the membrane is torn or missing.

The system, method, and device can independently test and hence compensate for and/or flag restriction of the membrane and the capillary using a single test. By using a pulse of test gas, a number of parameters can be measured, such as the total integrated charge (which may be the main measure for membrane restriction), the peak current (which may be the main measure for capillary restriction), and rates of rise and decay of the detected test gas pulse, which may also provide information regarding the time dependent movement of the gas.

By keeping the test gas pulse short and small, the risk of overloading the sensing electrode may be reduced and the sensing electrode may recover back to the normal operating mode within a short amount of time, such as less than one second. In some embodiments, the gas sensor can continue to detect target gas undisturbed (e.g., taking 1 reading per second) while the diagnostic mode is running.

As shown in FIG. 4, the gas sensor may be axially symmetrical. However, in some embodiments, the sensing electrode and the test gas electrode may be in various arrangements without deviating from the intent of the present disclosure. For instance, in FIG. 5, the gas sensor includes a test gas electrode on one end of the gas sensor and the sensing electrode on the other end of the gas sensor with the test gas diffusion path disposed between the two electrodes and open to the membrane between the two electrodes.

In some embodiments, the test gas electrode may be disabled when not generating test gas. In some embodiments, after generating a test gas pulse, the test gas electrode may be set to a potential where the test gas electrode may detect the test gas. In such embodiments, there are then two test gas detection transients (e.g., the total charge may still give the degree of membrane restriction, however, with two gas detection transients, more information may be obtained). In such embodiment, less of the test gas may diffuse into the bulk of the electrolyte where such diffusion could cause issues.

In some embodiments, a scavenging electrode in the electrolyte below the test gas electrode may be used. In some embodiments, the test gas electrode and the sensing electrodes may be in the same electrolyte (e.g., operated as a bipotentiostat with common counter and reference electrodes), while in some embodiments, the test gas electrode could be in a separate compartment with separate counter and reference electrodes and optionally a different electrolyte (e.g., an electrolyte specifically designed for test gas generation).

The disclosed systems, methods, and devices may be used in a variety of applications. For instance, the test gas electrode, where test gas is generated, may be used in non-electrochemical sensors such as pellistors.

The electrodes may be screen printed, automatically puddled on a substrate, such as a flexible tape, T-I, or combinations thereof. Various selective deposition techniques may be used, such as direct puddling, screen printing, or puddling onto a temporary support followed by press transfer. Conductors may be used to electrically connect each or several electrodes to circuitry 200. When more than one electrode is used, the electrodes may be of the same material or different materials. In some embodiments, the electrodes comprises one or more materials, such as platinum, iridium, ruthenium, gold, silver, carbon, or combinations thereof. For instance, catalyst materials for either the sensing electrode or test gas electrode may include platinum, iridium, ruthenium, gold, silver, carbon, or mixtures of these. In some embodiments, the sensing electrode may detect both the target gas and the test gas. In some embodiments, the sensing electrode and test gas electrode comprise the same material.

The membrane may comprise any suitable material, such as polytetrafluoroethylene (PTFE), and may include any suitable mesh size. The materials and construction of the membrane may vary based on the intended application of the gas sensor. The gas sensor may be used to detect a single target gas, two target gases, or a plurality of target gases. The gas sensor may also monitor the temperature, pressure, location, and movement of the gas sensor and environment in which the gas sensor is located (e.g., the "external environment").

While one or more electrodes are operating as disclosed herein, one or more other electrodes may be performing different functions, such as being treated electrochemically for remediation purposes. Circuitry 200 may switch, activate, or deactivate electrodes, both for sensing a target gas and sensing a test gas. Multiple reference or counter electrodes can be provided. One benefit to the use of multiple electrodes is that there is built in redundancy due to the use of multiple sensing electrodes. Since these can be operated alternatively, any poisoning or degradation processes may occur differently on the different electrodes and hence drift in performance can be detected by comparison of the responses on the various electrodes. U.S. Application Publication No. 2013/087457 describes gas sensors and electrodes and is incorporated herein in its entirety.

Methods, apparatuses, systems, and computer program products of the present invention may be embodied by any of a variety of devices. For example, the method, apparatus, systems, and computer program product of an example embodiment may be embodied by a networked device (e.g., an enterprise platform), such as a server or other network entity, configured to communicate with one or more devices, such as gas sensors. Additionally or alternatively, the system may include fixed computing devices, such as a personal computer or a computer workstation. Still further, example embodiments may be embodied by any of a variety of mobile devices, such as a portable digital assistant (PDA), mobile telephone, smartphone, laptop computer, tablet computer, wearable, or any combination of the aforementioned devices.

In some embodiments, the circuitry 200 and/or gas sensory system 100 described herein may be embodied in a single self-contained portable or fixed gas sensor. For instance, in some embodiments, all of the functionality and processing described herein may be incorporated into a gas sensor itself as an intelligent sensor module which provides a completely processed digital output to the instrument (e.g., ASICS and embedded processors are sufficiently powerful).

FIG. 1 shows gas sensor system 100 including an example network architecture for a system, which may include one or more devices and sub-systems that are configured to implement some embodiments discussed herein. For example, gas sensor system 100 may include server 140 and/or client device 130, which can include, for example, the circuitry disclosed in FIGS. 2-3B, a server, or database, among other things (not shown). The server 140 and/or client device 130 may include any suitable network server and/or other type of computing device. In some embodiments, the server 140 and/or client device 130 may receive, determine, and transmit alarms, data, and instructions to gas sensor 400A-400N using data from the gas restriction detection database 300. The gas restriction detection database 300 (shown e.g., in FIGS. 3A and 3B) may be embodied as a data storage device such as a Network Attached Storage (NAS) device or devices, or as a separate database server or servers. The gas restriction detection database 300 includes information accessed and stored by the server 140 and/or client device 130 to facilitate the operations of the gas sensor system 100. For example, the gas restriction detection database 300 may include, without limitation, a plurality of sensing electrode data, telemetry data, application data, test gas data, test gas electrode data, gas sensor data, etc.

Server 140 and/or client device 130 can communicate with one or more gas sensors 400A-400N via communications network 120. In this regard, communications network 120 may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, etc.). For example, communications network 120 may include a cellular telephone, an 802.11, 802.16, 802.20, and/or WiMax network. Further, the communications network 120 may include a public network, such as the Internet, a private network, such as an intranet, or combinations thereof, and may utilize a variety of networking protocols now available or later developed including, but not limited to TCP/IP based networking protocols. For instance, the networking protocol may be customized to suit the needs of the gas restriction detection system.

The server 140 and/or client device 130 may provide for receiving of electronic data from various sources, including but not necessarily limited to the gas sensors 400A-400N. For example, the server 140 and/or client device 130 may be operable to receive or transmit sensing electrode data, telemetry data, application data, test gas data, test gas electrode data, gas sensor data provided by the gas sensors 400A-400N.

Gas sensors 400A-400N, server 140, and/or client device 130 may each be implemented using a personal computer and/or other networked device, such as a cellular phone, tablet computer, mobile device, inventory management terminal etc. that may be used for any suitable purpose in addition to monitoring the gas sensors. The depiction in FIG. 1 of "N" devices is merely for illustration purposes. Any number of gas sensors may be included in the gas sensor system 100. In one embodiment, the gas sensors 400A-400N may be configured to view, create, edit, and/or otherwise interact with target gas information, test gas information, and/or telemetry data of the gas sensor, system, and/or environment in which the gas sensor is located, which may be provided by the client device 130, server 140, gas sensors 400A-400N, or other devices in the gas sensor system 100. According to some embodiments, the server 140 and/or client device 130 may be configured to display the test gas information and/or telemetry data on a display of the server 140 and/or client device 130 for viewing, creating, editing, and/or otherwise interacting with the data. In some embodiments, an interface of a gas sensor 400A-400N may be different from an interface of a server 140 and/or client device 130. The gas sensors 400A-400N may be used in addition to or instead of the server 140 and/or client device 130. Gas sensor system 100 may also include additional client devices and/or servers, among other things. Additionally or alternatively, the gas sensor 400A-400N may interact with the gas sensor system 100 via a web browser. As yet another example, the gas sensor 400A-400N may include various hardware or firmware designed to interface with the gas sensor system 100.

In some embodiments, the gas sensors 400A-400N are electrochemical gas sensors. In some embodiments, the gas sensors 400A-400N may include any computing device as defined above. Electronic data received by the server 140 and/or client device 130 from the gas sensors 400A-400N may be provided in various forms and via various methods. In some embodiments, the gas sensors 400A-400N, server 140, and client device 130 may include mobile devices, wearables, and the like.

In embodiments where the client device 130 and/or server 140 is a mobile device, such as a smart phone or tablet, the server 140 and/or client device 130 may execute an "app" to interact with the gas sensor system 100. Such apps are typically designed to execute on mobile devices, such as tablets or smartphones. For example, an app may be provided that executes on mobile device operating systems such as iOS®, Android®, or Windows®. These platforms typically provide frameworks that allow apps to communicate with one another and with particular hardware and software components of mobile devices. For example, the mobile operating systems named above each provide frameworks for interacting with location services circuitry, wired and wireless network interfaces, user contacts, and other applications. Communication with hardware and software modules executing outside of the app is typically provided via application programming interfaces (APIs) provided by the mobile device operating system.

In some embodiments of an exemplary gas sensor system 100, information may be sent from a gas sensor 400A-400N to the server 140 and/or client device 130. In various implementations, the information may be sent to the gas sensor system 100 over communications network 120 directly by a gas sensor 400A-400N, the information may be sent to the gas sensor system 100 via an intermediary such as a another client device, server, and/or the like. For example, the gas sensor 400A-400N may communicate with a desktop, a laptop, a tablet, a smartphone, and/or the like that is executing a client application to interact with the gas sensor system 100. In one implementation, the information may include data such as sensing electrode data, telemetry data, application data, test gas data, test gas electrode data, gas sensor data, and/or the like.

The gas sensor system 100 may comprise at least one server 140 and/or client device 130 that may create a storage data entry based upon the received information to facilitate indexing and storage in a gas restriction detection database 300, as will be described further below. In one implementation, the storage data entry may include data such as sensing electrode data, telemetry data, application data, test gas data, test gas electrode data, gas sensor data, and/or the like.

In one implementation, the sensing electrode data, telemetry data, application data, test gas data, test gas electrode data, gas sensor data, and/or the like may be parsed (e.g., using PHP commands) to determine information regarding the gas sensor, specifically the electrodes, membrane(s), capillary, test gas, external environment in which the gas sensor is located, etc.

Figure 2:
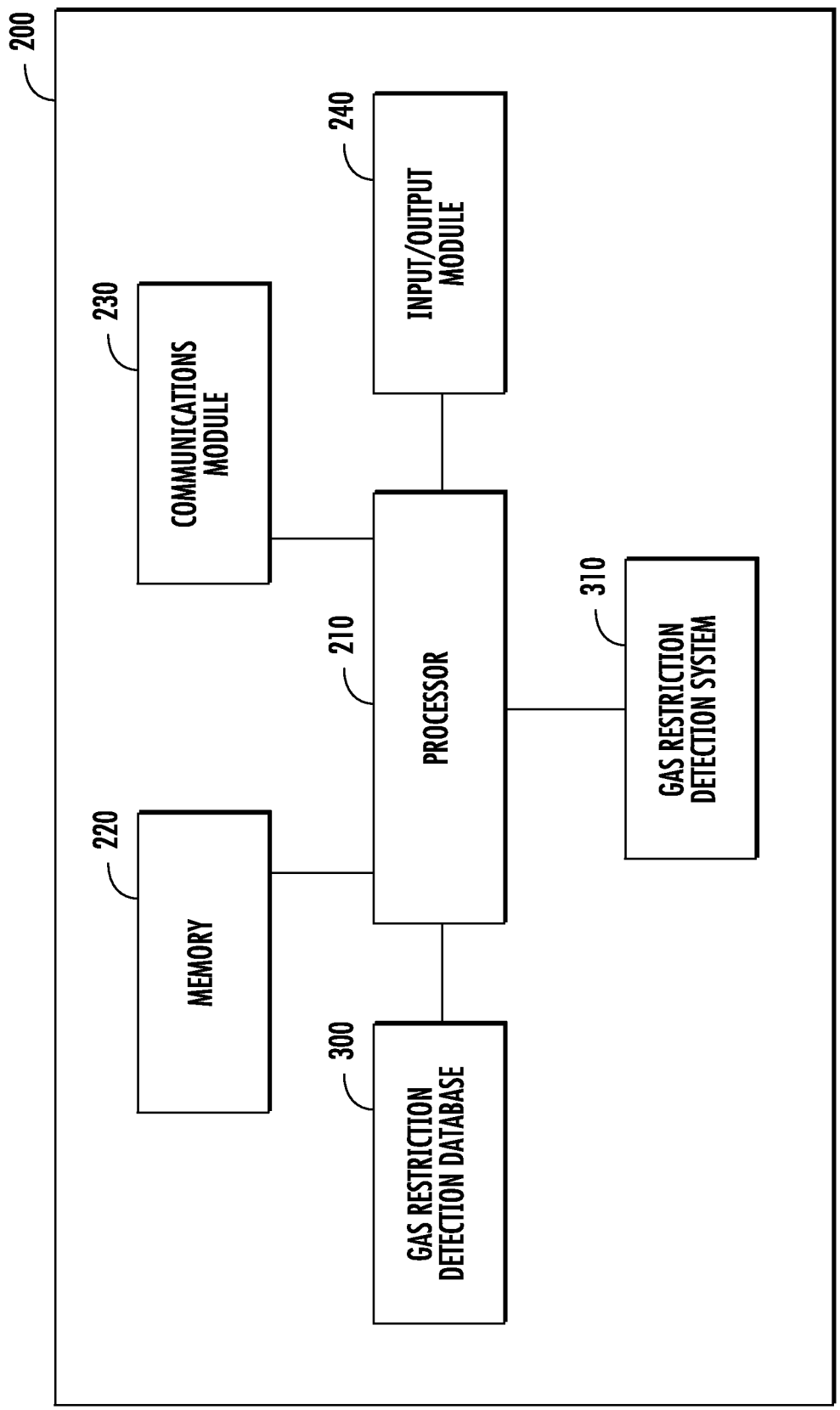
FIG. 2 illustrates a schematic block diagram of circuitry that can be included in a device in accordance with some embodiments discussed herein.
Figure 3A:
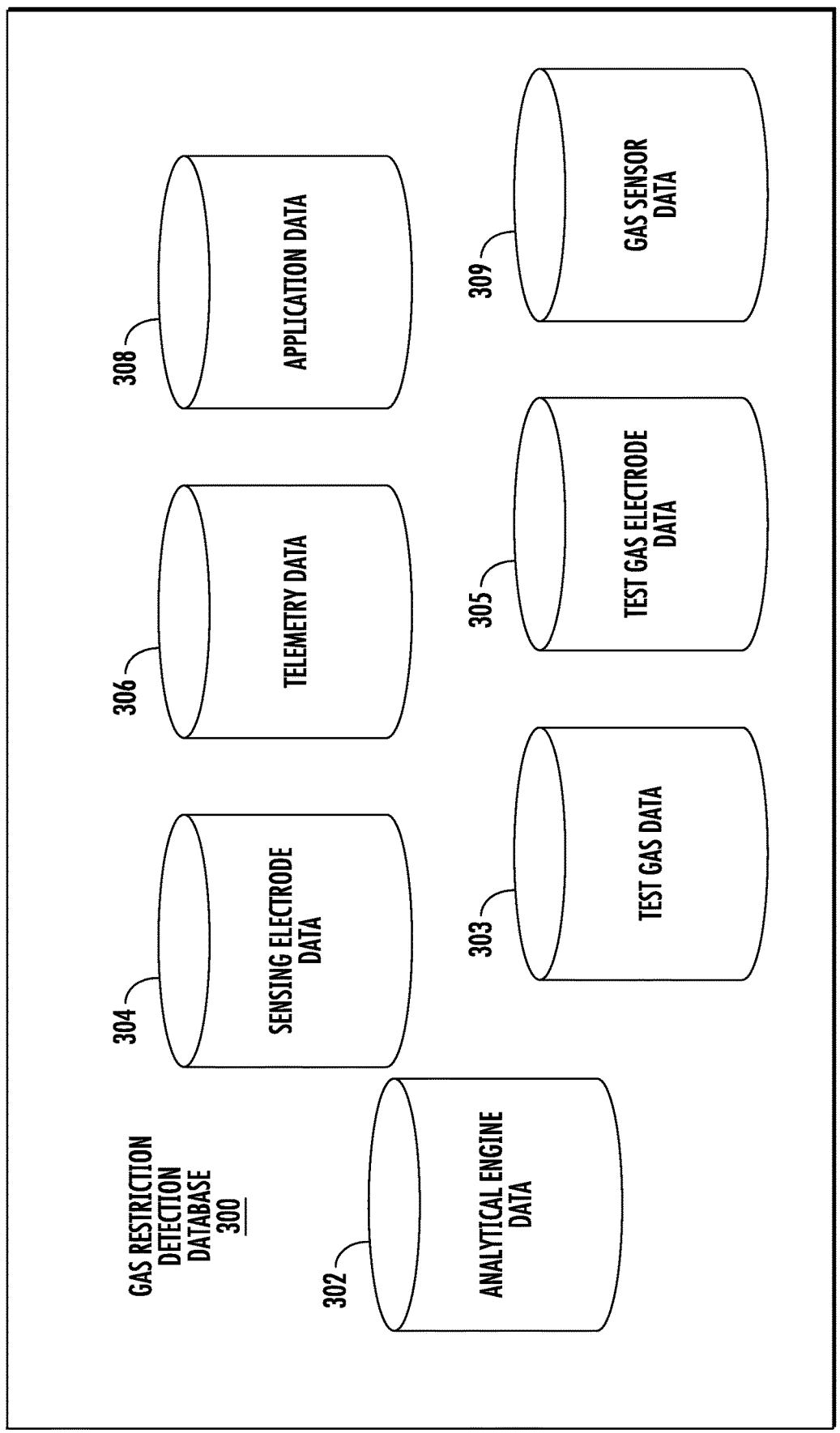
FIG. 3A illustrates an example gas restriction detection database in accordance with some embodiments discussed herein.

FIG. 2 shows a schematic block diagram of circuitry 200, some or all of which may be included in, for example, server 140, client device 130, and/or gas sensors 400A-400N. Any of the aforementioned server 140, client device 130, and/or gas sensors 400A-400N may include one or more components of circuitry 200 and may be configured to, either independently or jointly with other devices in the communications network 120 perform the functions of the circuitry 200 described herein. As illustrated in FIG. 2, in accordance with some example embodiments, circuitry 200 can includes various means, such as processor 210, memory 220, communications module 230, and/or input/output module 240. In some embodiments, gas restriction detection database 300 may also or instead be included. As referred to herein, "module" includes hardware, software and/or firmware configured to perform one or more particular functions. In this regard, the means of circuitry 200 as described herein may be embodied as, for example, circuitry, hardware elements (e.g., a suitably programmed processor, combinational logic circuit, and/or the like), a computer program product comprising computer-readable program instructions stored on a non-transitory computer-readable medium (e.g., memory 220) that is executable by a suitably configured processing device (e.g., processor 210), or some combination thereof.

Processor 210 may, for example, be embodied as various means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an ASIC (application specific integrated circuit) or FPGA (field programmable gate array), or some combination thereof. Accordingly, although illustrated in FIG. 2 as a single processor, in some embodiments processor 210 comprises a plurality of processors. The plurality of processors may be embodied on a single server 140, client device 130, and/or gas sensor 400A-400N or may be distributed across a plurality of such devices collectively configured to function as circuitry 200. The plurality of processors may be in operative communication with each other and may be collectively configured to perform one or more functionalities of circuitry 200 as described herein. In an example embodiment, processor 210 is configured to execute instructions stored in memory 220 or otherwise accessible to processor 210. These instructions, when executed by processor 210, may cause circuitry 200 to perform one or more of the functionalities of circuitry 200 as described herein.

Whether configured by hardware, firmware/software methods, or by a combination thereof, processor 210 may comprise an entity capable of performing operations according to embodiments of the present invention while configured accordingly. Thus, for example, when processor 210 is embodied as an ASIC, FPGA or the like, processor 210 may comprise specifically configured hardware for conducting one or more operations described herein. Alternatively, as another example, when processor 210 is embodied as an executor of instructions, such as may be stored in memory 220, the instructions may specifically configure processor 210 to perform one or more algorithms and operations described herein, such as those discussed in connection with FIG. 12.

Memory 220 may comprise, for example, volatile memory, non-volatile memory, or some combination thereof. Although illustrated in FIG. 2 as a single memory, memory 220 may comprise a plurality of memory components. The plurality of memory components may be embodied on a single server 140, client device 130, and/or gas sensor 400A-400N or distributed across a plurality of such devices. In various embodiments, memory 220 may comprise, for example, a hard disk, random access memory, cache memory, flash memory, a compact disc read only memory (CD-ROM), digital versatile disc read only memory (DVD-ROM), an optical disc, circuitry configured to store information, or some combination thereof. Memory 220 may be configured to store information, data (including data discussed with regards to gas restriction detection database 300), applications, instructions, or the like for enabling circuitry 200 to carry out various functions in accordance with example embodiments of the present invention. For example, in at least some embodiments, memory 220 is configured to buffer input data for processing by processor 210. Additionally or alternatively, in at least some embodiments, memory 220 is configured to store program instructions for execution by processor 210. Memory 220 may store information in the form of static and/or dynamic information. This stored information may be stored and/or used by circuitry 200 during the course of performing its functionalities.

Communications module 230 may be embodied as any device or means embodied in circuitry, hardware, a computer program product comprising computer readable program instructions stored on a computer readable medium (e.g., memory 220) and executed by a processing device (e.g., processor 210), or a combination thereof that is configured to receive and/or transmit data from/to another device and/or network, such as, for example, a second circuitry 200 and/or the like. In some embodiments, communications module 230 (like other components discussed herein) can be at least partially embodied as or otherwise controlled by processor 210. In this regard, communications module 230 may be in communication with processor 210, such as via a bus. Communications module 230 may include, for example, an antenna, a transmitter, a receiver, a transceiver, network interface card and/or supporting hardware and/or firmware/software for enabling communications with another device of the gas sensor system 100. Communications module 230 may be configured to receive and/or transmit any data that may be stored by memory 220 using any protocol that may be used for communications between devices of the gas sensor system 100. Communications module 230 may additionally or alternatively be in communication with the memory 220, input/output module 240 and/or any other component of circuitry 200, such as via a bus.

Circuitry 200 may include input/output module 240 in some embodiments. Input/output module 240 may be in communication with processor 210 to receive an indication of a user input and/or to provide an audible, visual, mechanical, or other output to a user. As such, input/output module 240 may include support, for example, for a keyboard, a mouse, a joystick, a display, a touch screen display, a microphone, a speaker, a RFID reader, barcode reader, biometric scanner, and/or other input/output mechanisms. In embodiments wherein circuitry 200 is embodied as a server or database, aspects of input/output module 240 may be reduced as compared to embodiments where circuitry 200 is implemented as an end-user machine or other type of device designed for complex user interactions. In some embodiments (like other components discussed herein), input/output module 240 may even be eliminated from circuitry 200. Alternatively, such as in embodiments wherein circuitry 200 is embodied as a server or database, at least some aspects of input/output module 240 may be embodied on an apparatus used by a user that is in communication with circuitry 200. Input/output module 240 may be in communication with the memory 220, communications module 230, and/or any other component(s), such as via a bus. One or more than one input/output module and/or other component can be included in circuitry 200.

Gas restriction detection database 300 and gas restriction detection system 310 may also or instead be included and configured to perform the functionality discussed herein related to storing, generating, and/or editing data. In some embodiments, some or all of the functionality of storing, generating, and/or editing data may be performed by processor 210. In this regard, the example processes and algorithms discussed herein can be performed by at least one processor 210, gas restriction detection database 300, and/or gas restriction detection system 310. For example, non-transitory computer readable media can be configured to store firmware, one or more application programs, and/or other software, which include instructions and other computer-readable program code portions that can be executed to control each processor (e.g., processor 210, gas restriction detection database 300, and gas restriction detection system 310) of the components of circuitry 200 to implement various operations, including the examples shown above. As such, a series of computer-readable program code portions are embodied in one or more computer program goods and can be used, with a computing device, server, and/or other programmable apparatus, to produce machine-implemented processes.

In some embodiments, a gas restriction detection database 300 may be provided that includes sensing electrode data 304, telemetry data 306, application data 308, test gas data 303, test gas electrode data 305, gas sensor data 309, and/or analytical engine data 302. Sensing electrode data 304 may include various information, such as type of electrode, expected life of electrode, date of first use of electrode, relative location of electrode in gas sensor 400A-400N, and any other information concerning the sensing electrode. Telemetry data 306 may include various information, such as measurements of temperature, pressure, motion, and the like, which may be measured periodically, at certain dates, or on command. Application data 308 may include various information specific to the application in which the gas sensor 400A-400N is used, such as typical or expected telemetry data, gas sensor data, location data, or other data related to the application in which the gas sensor 400A-400N is used. Test gas data 303 may include various information, such as type of gas(es) used as the test gas, amount of generated test gas, test gas pulse duration, diagnostic intervals (that is, period of time between diagnostic testing), and other data related to the test gas. Test gas electrode data 304 may include various information, such as type of electrode, expected life of electrode, date of first use of electrode, relative location of electrode in gas sensor 400A-400N, and any other information concerning the test gas electrode. Gas sensor data 309 may include various information, such as make/model/serial number of sensor, type of sensor, expected life of sensor, date of first use of sensor, history of maintenance of sensor, expected date(s) of maintenance of sensor, relative location of sensor in environment, limits on gas sensor readings, and any other information concerning the gas sensor 400A-400N and use of the gas sensor 400A-400N. Additionally or alternatively, the gas restriction detection database 300 may include analytical engine data 302 which provides any additional information needed by the processor 210 in storing, analyzing, generating, and editing data.

Gas restriction detection system 310 can be configured to analyze multiple sets of data, such as the data in the gas restriction detection database 300. In this way, gas restriction detection system 310 may support multiple algorithms, including those discussed below with respect to sensing electrode data 304, telemetry data 306, application data 308, test gas data 303, test gas electrode data 305, gas sensor data 309, and/or analytical engine data 302, so that the selected algorithm may be chosen at runtime. Further, the present configuration can enable flexibility in terms of configuring additional contexts.

Figure 3B:
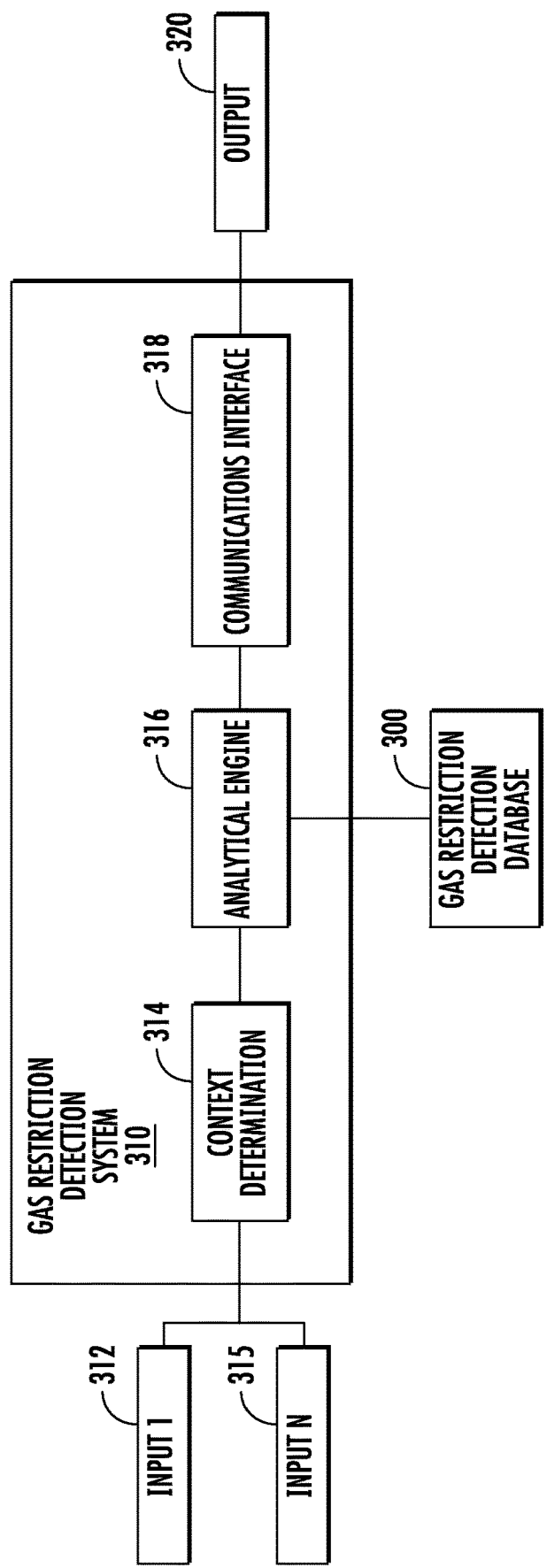
FIG. 3B illustrates an example gas restriction detection system in accordance with some embodiments discussed herein.

In some embodiments, with reference to FIG. 3B, the gas restriction detection system 310 may include a context determination module 314, an analytical engine 316, and communications interface 318, all of which may be in communication with the gas restriction detection database 300. The gas restriction detection system 310 may receive one or more signals (e.g., test gas signals, target gas signals, interrogation signals, response signals, instructions, etc.) that may contain information such as sensing electrode data 304, telemetry data 306, application data 308, test gas data 303, test gas electrode data 305, gas sensor data 309, etc. and may generate the appropriate signals that may contain information such as sensing electrode data 304, telemetry data 306, application data 308, test gas data 303, test gas electrode data 305, gas sensor data 309, etc. in response. The gas restriction detection system 310 may use any of the algorithms or processes disclosed herein for receiving one or more signals (e.g., test gas signals, target gas signals, interrogation signals, response signals, instructions, etc.) that may contain information such as sensing electrode data 304, telemetry data 306, application data 308, test gas data 303, test gas electrode data 305, gas sensor data 309, etc. and may generate the appropriate signals that may contain information such as sensing electrode data 304, telemetry data 306, application data 308, test gas data 303, test gas electrode data 305, gas sensor data 309, etc. in response. In some other embodiments, such as when the circuitry 200 is embodied in a server 140, client device 130, and/or gas sensors 400A-400N, the gas restriction detection system 310 may be located in another circuitry 200 or another device, such as another server 140, client device 130, gas sensors 400A-400N, and/or other client device.

The gas restriction detection system 310 can be configured to access data corresponding to multiple signals (e.g., interrogation signals, response signals, etc.) that may contain information such as sensing electrode data 304, telemetry data 306, application data 308, test gas data 303, test gas electrode data 305, gas sensor data 309, etc. and may generate the appropriate signals that may contain information such as sensing electrode data 304, telemetry data 306, application data 308, test gas data 303, test gas electrode data 305, gas sensor data 309, etc. in response.

The system may receive a plurality of inputs 312, 315 from the circuitry 200 and process the inputs within the gas restriction detection system 310 to produce an output 320, which may include signals containing appropriate information in response. In some embodiments, the gas restriction detection system 310 may execute context determination using the context determination module 314, process the data in an analytical engine 316, and output the results via a communications interface 318. Each of these steps may pull data from a plurality of sources including the gas restriction detection database 300.

When inputs 312, 315 are received by the gas restriction detection system 310, a context determination using the context determination module 314 may be made. A context determination includes such information as application data, what gas sensor 400A-400N initiated receipt of the input, what type of input was provided (e.g., were test gas signals, target gas signals, interrogation signals, response signals, instructions, etc. received) and under what circumstances was receipt of the input initiated (e.g., where is the gas sensor 400A-400N located, when was the input received, what signal or receipt of information preceded the input, etc.). This information may give context to the gas restriction detection system 310 analysis to determine the output. For example, the context determination module 314 may inform the gas restriction detection system 310 as to the signal and/or information to output.

The gas restriction detection system 310 may then compute the output using the analytical engine 316. The analytical engine 316 draws information about the applicable signal, gas sensor 400A-400N, etc. from the gas restriction detection database 300 and then, in light of the context determination module's 314 determination, computes an output, which varies based on the input. The communications interface 318 then outputs 320 the output to the circuitry 200 for storing, displaying on an appropriate interface, transmitting to other devices or server(s), or otherwise using for subsequent action. For instance, the context determination module 314 may determine that a test gas signal was received. Based on this information as well as the applicable gas sensor data, telemetry data, sensing electrode data, application data, test gas data, test gas electrode data, etc., the analytical engine 316 may determine an appropriate output, such as displaying an alarm that the membrane or capillary associated with the gas sensor 400A-400N associated with the test gas signal is in need of maintenance. The analytical engine 316 may receive a target gas signal. Based on this information as well as the applicable gas sensor data, telemetry data, sensing electrode data, application data, test gas data, test gas electrode data, etc., the analytical engine 316 may determine that gas sensor 400A-400N should be switched from diagnostic mode to normal operating mode where target gas is monitored. The gas sensor 400A-400N may then have the generation of test gas disabled allowing for monitoring of the target gas. Based on the applicable gas sensor data, telemetry data, sensing electrode data, application data, test gas data, test gas electrode data, etc., the analytical engine 316 may determine that a certain period of time has passed since the last diagnostic test. Circuitry 200 may then cause test gas to flow through the test gas diffusion path in the appropriate gas sensor 400A-400N.

As will be appreciated, any such computer program instructions and/or other type of code may be loaded onto a computer, processor or other programmable apparatus's circuitry to produce a machine, such that the computer, processor other programmable circuitry that execute the code on the machine create the means for implementing various functions, including those described herein.

It is also noted that all or some of the information discussed herein can be based on data that is received, generated, and/or maintained by one or more components of a local or networked system and/or circuitry 200. In some embodiments, one or more external systems (such as a remote cloud computing and/or data storage system) may also be leveraged to provide at least some of the functionality discussed herein.

As described above and as will be appreciated based on this disclosure, embodiments of the present invention may be configured as methods, personal computers, servers, mobile devices, backend network devices, and the like. Accordingly, embodiments may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices.

Embodiments of the present invention have been described above with reference to block diagrams and flowchart illustrations of methods, apparatuses, systems and computer program goods. It will be understood that each block of the circuit diagrams and process flowcharts, and combinations of blocks in the circuit diagrams and process flowcharts, respectively, can be implemented by various means including computer program instructions. These computer program instructions may be loaded onto a general purpose computer, special purpose computer, or other programmable data processing apparatus, such as processor 210, gas restriction detection database 300, and/or gas restriction detection system 310 discussed above with reference to FIG. 2, to produce a machine, such that the computer program product includes the instructions which execute on the computer or other programmable data processing apparatus create a means for implementing the functions specified in the flowchart block or blocks.

These computer program instructions may also be stored in a computer-readable storage device (e.g., memory 220) that can direct a computer or other programmable data processing apparatus to function in a particular manner, such that the instructions stored in the computer-readable storage device produce an article of manufacture including computer-readable instructions for implementing the function discussed herein. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions discussed herein.

Accordingly, blocks of the block diagrams and flowchart illustrations support combinations of means for performing the specified functions, combinations of steps for performing the specified functions and program instruction means for performing the specified functions. It will also be understood that each block of the circuit diagrams and process flowcharts, and combinations of blocks in the circuit diagrams and process flowcharts, can be implemented by special purpose hardware-based computer systems that perform the specified functions or steps, or combinations of special purpose hardware and computer instructions.

FIGS. 4A-12 discuss gas sensor 400 which may be any one or more of gas sensors 400A-400N of gas sensor system 100.

Figure 4A:
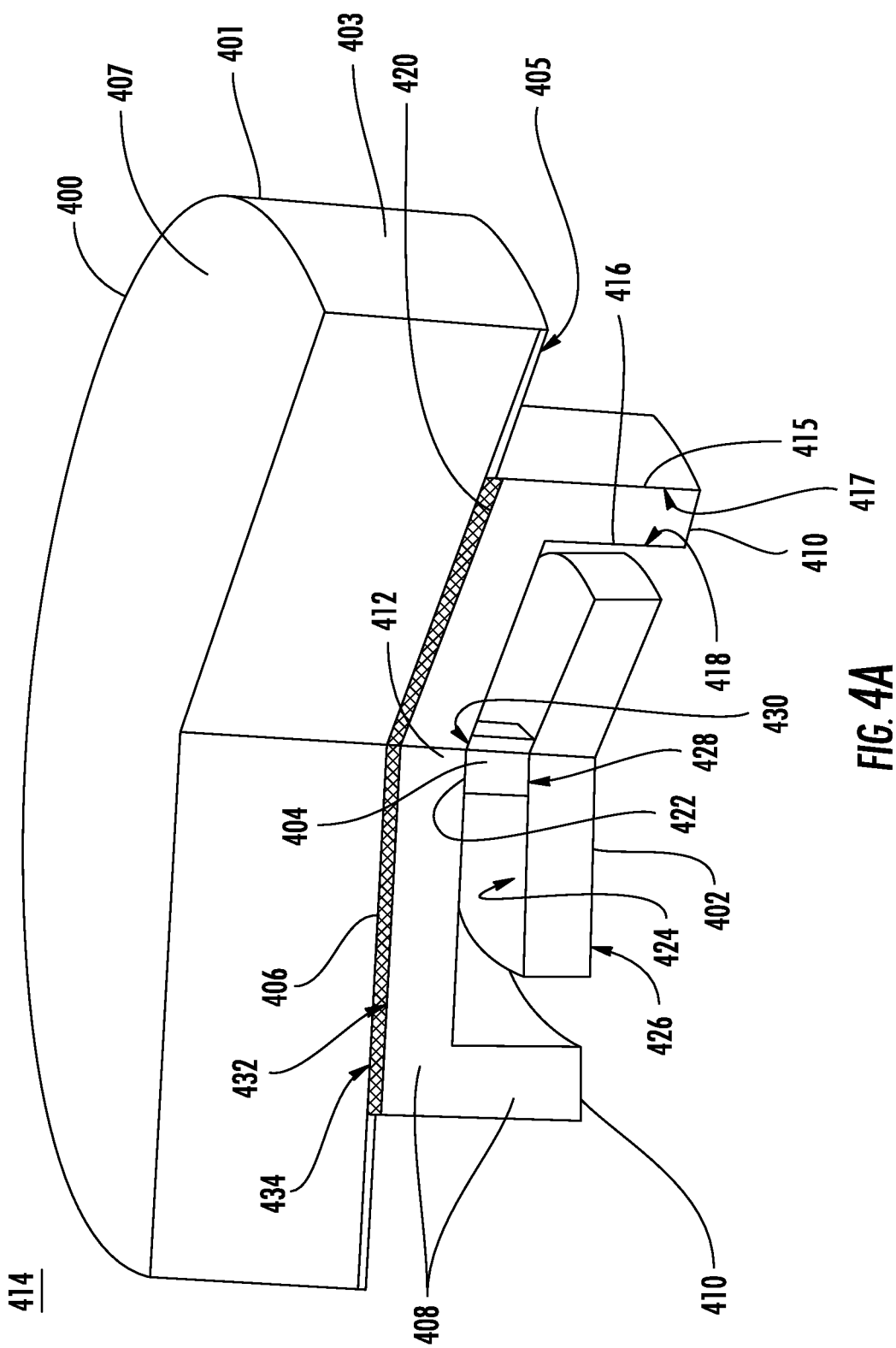
FIGS. 4A and 4B provide a cross section of an example gas sensor in accordance with some embodiments discussed herein.

FIG. 4A illustrates an example gas sensor in accordance with some embodiments of the present disclosure. In particular, FIG. 4A illustrates a cross-section of a gas sensor 400 including a housing 401 including housing wall 403 that defines an opening 407 in the housing 401 to the external environment 414. The housing 401 also includes a second housing wall 405. The gas sensor 400 includes a sensing electrode 402, a capillary 404, a membrane 406, and a test gas diffusion path 408. The test gas diffusion path 408 has an inlet 410 and an outlet 412. The test gas enters the test gas diffusion path 408 at the inlet 410 and exits the test gas diffusion path at the outlet 412. In the embodiment illustrated in FIG. 4A, following the outlet 412, the test gas enters the capillary 404 and then comes in contact with the sensing electrode 402. In some embodiments, a capillary 404 is not present. In such embodiments, the test gas comes in contact with the sensing electrode 402 at the outlet 412 of the test gas diffusion path 408.

In the embodiment illustrated in FIG. 4A, the test gas diffusion path 408 includes a first wall 415 and a second wall 416 defining the test gas diffusion path 408 for the test gas to travel through the gas sensor 400. The first wall 415 and the second wall 416 may each have an inner surface 417 and 418, respectively and may define a first test gas diffusion path opening 420 that exposes the test gas to the membrane 406 and a second test gas diffusion path opening 422 that exposes the test gas to the capillary 404 and sensing electrode 402. For instance, in the embodiment illustrated in FIG. 4A, the test gas diffusion path 408 includes a first wall 415 that defines a first test gas diffusion path opening 420 that exposes the test gas traveling through the test gas diffusion path 408 to the membrane 406. The second wall 416 defines a second test gas diffusion path opening 422 that exposes the test gas traveling through the test gas diffusion path 408 to the capillary 404. As shown in FIG. 4A, the test gas diffusion path 408 is defined by two walls, however, additional walls may be present, such as a third and fourth wall, without deviating from the intent of the present disclosure. Also, as shown in FIG. 4A, the outlet 412 of the test gas diffusion path 408 is also the second test gas diffusion path opening 422.

The sensing electrode 402 may include various materials suitable for sensing a target gas as well as a test gas, which may be the same or different from the target gas. The sensing electrode 402 may have a first surface 424 and a second surface 426. In the embodiment illustrated in FIG. 4A, the first surface 424 is proximal to the capillary 404 and the second surface 426 is distal to the capillary 404. The capillary 404 includes a first end 430 and a second end 428. The first end 430 of the capillary 404 is exposed to the test gas by way of the second test gas diffusion path opening 422 of the second wall 416 of the test gas diffusion path 408. The second end 428 of the capillary 404 is adjacent to the sensing electrode 402.

The membrane 406 of the gas sensor 400 includes a first surface 432 and a second surface 434. The second surface 434 of the membrane 406 is exposed to the external environment 414 while the first surface 432 is exposed to the test gas by way of the first test gas diffusion path opening 420 of the first wall 415 of the test gas diffusion path 408.

As shown in FIG. 4A, the first test gas diffusion path opening 420 is disposed prior to the second test gas diffusion path opening 422 along the test gas diffusion path 408 in the direction of flow from the inlet 410 of the test gas diffusion path 408 to the outlet 412 of the test gas diffusion path 408. As test gas travels through the test gas diffusion path 408, the test gas comes in contact with the membrane 406, particularly the first surface 432 of the membrane 406, then the capillary 404, and then the sensing electrode 402. If the membrane 406 is clean, that is, does not include any blockage in the pores of the membrane, then some of the test gas would travel through the membrane 406 to the external environment 414. Some test gas may travel to the capillary 404 and the sensing electrode 402. If the membrane 406 is damaged or missing, most of the test gas may be released to the external environment 414 and the sensing electrode 402 may detect a minor amount of test gas if any. If the membrane 406 includes blockage, such as dirt or debris, the test gas will be prevented from traveling through the membrane 406 and instead proceed on to the capillary 404 and then the sensing electrode 402. If the capillary 404 is clean, the test gas will travel quickly to the sensing electrode 402. If the capillary 404 is blocked, the test gas will travel as a slower pace to the sensing electrode 402. Accordingly, the test gas signal produced by the sensing electrode 402 can be used to determine the degree of restriction of the membrane 406 and the capillary 404 due to the test gas diffusion path 408. The total amount of test gas detected at the sensing electrode 402 may provide the degree of restriction of the membrane 406 and the magnitude of the test gas signal produced at the sensing electrode 402 may provide the degree of restriction of the capillary 404. Accordingly, the status of the gas sensor 400 can be monitored.

Test gas may be caused to travel through the test gas diffusion path 408 at various intervals, such as about every 5 minutes, 10 minutes, 20 minutes, 30 minutes, 45 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours 16 hours, 17 hours, 18 hours, 19 hours, 20 hours, 21 hours, 22 hours, 23 hours, 24 hours, 36 hours, 48 hours, 72 hours, etc. In some embodiments, the test gas may be caused to travel through the test gas diffusion path 408 as needed or on demand. That is, an operator may determine when the diagnostic test is needed and cause the test gas to travel through the test gas diffusion path 408.

With the disclosed test gas diffusion path 408 and diagnostic mode, the condition of the membrane 406 and the capillary 404 may be monitored. Early detection of blockage or cuts/tears in the membrane 406 may be obtained as well as early detection of blockage of the capillary 404. Accordingly, the gas sensor 400 may receive the appropriate maintenance. The life of the gas sensor 400 may be extended with such appropriate maintenance.

As shown in the embodiment illustrated in FIG. 4A, as the test gas enters the test gas diffusion path 408 and moves through the test gas diffusion path 408, the test gas comes in contact with the membrane 406. In the embodiment illustrated in FIG. 4, the membrane 406 covers the test gas diffusion path 408 and the sensing electrode 402 from the external environment 414.

Figure 4B:
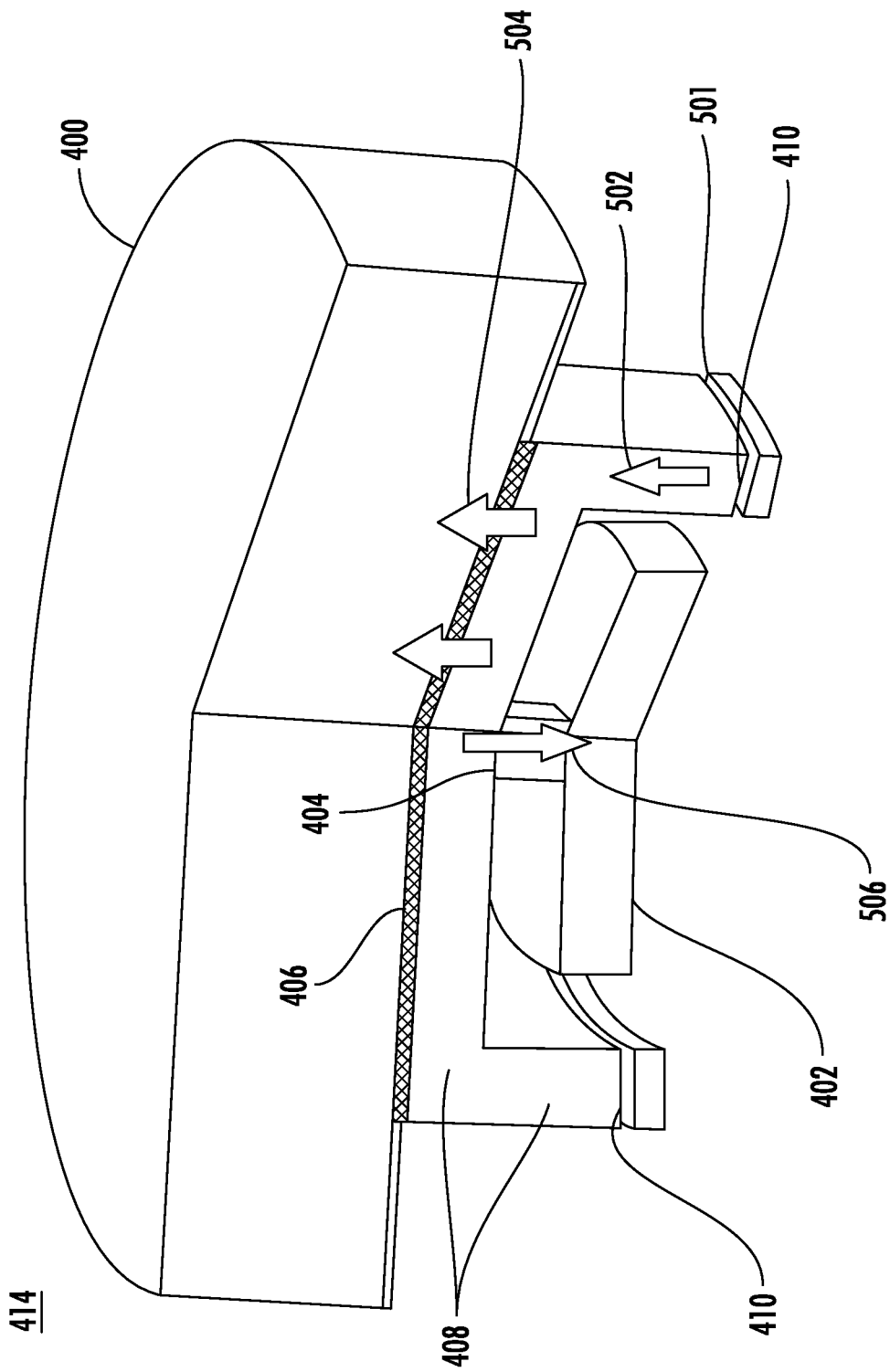

In the embodiments illustrated in FIG. 4A, test gas enters the inlet 410 of the test gas diffusion path 408. Test gas may be generated by the gas sensor 400 and then enter the test gas diffusion path 408 at the inlet 410 or may be applied to the gas sensor 400 from an external source and enter the test gas diffusion path 408 at the inlet 410. For instance, FIG. 4B illustrates a test gas electrode 501 that may be integrated into the gas sensor 400 or may be an external test gas generator operatively coupled to the gas sensor 400 when test gas is needed or desired. For instance, the test gas electrode 501 may be disposed within the housing 401 or may be disposed in an external housing that can then be connected to the gas sensor 400 to allow the test gas to enter the inlet 410 of the test gas diffusion path 408. The test gas electrode 501 may include the same or different materials and dimensions as the sensing electrode 402. The same or different electrolyte may be used with the sensing electrode 402 and the test gas electrode 501 to generate test gas.

In some embodiments, the same electrode (e.g., sensing electrode 402 or test gas electrode 501) may be used to generate the test gas and then detect test gas. In such embodiments, the electrode (e.g., sensing electrode 402 or test gas electrode 501) may require time to settle since there may be a large current transient when the potential is changed. In addition, in such embodiments, there may be more of a risk of test gas getting into the bulk solution and causing slow recovery.

FIG. 4B illustrates the flow of test gas in a gas sensor in accordance with some embodiments disclosed herein. In particular, FIG. 4B illustrates gas sensor 400 including membrane 406, capillary 404, test gas diffusion path 408, and sensing electrode 402, such as those described in accordance with FIG. 4A. The flow of test gas is shown by arrows 502, 504, and 506. At the inlet 410 of the test gas diffusion path 408, test gas enters 502 the test gas diffusion path 408. Test gas then proceeds through the test gas diffusion path 408 and is exposed to the membrane 406. Test gas exits 504 the gas sensor 400 through the membrane 406 if able to. That is, if the membrane 406 is not sufficiently blocked, then test gas exits 504 through the membrane 406. The remainder test gas 506 enters the capillary 404 and flows to the sensing electrode 402, where the remainder test gas 506 is detected and analyzed (e.g., by circuitry 200).

As in FIG. 4A, the gas sensor 400 shown in the embodiment illustrated in FIG. 4B is concentric with the sensing electrode 402 disposed in the middle of the gas sensor 400 and the test gas diffusion path 408 disposed around the sensing electrode 402. The membrane 406 is disposed above the capillary 404 and sensing electrode 402. The gas sensor 400 is axially symmetrical. However, various geometries and configurations are available without deviating from the present disclosure.

Figure 5:
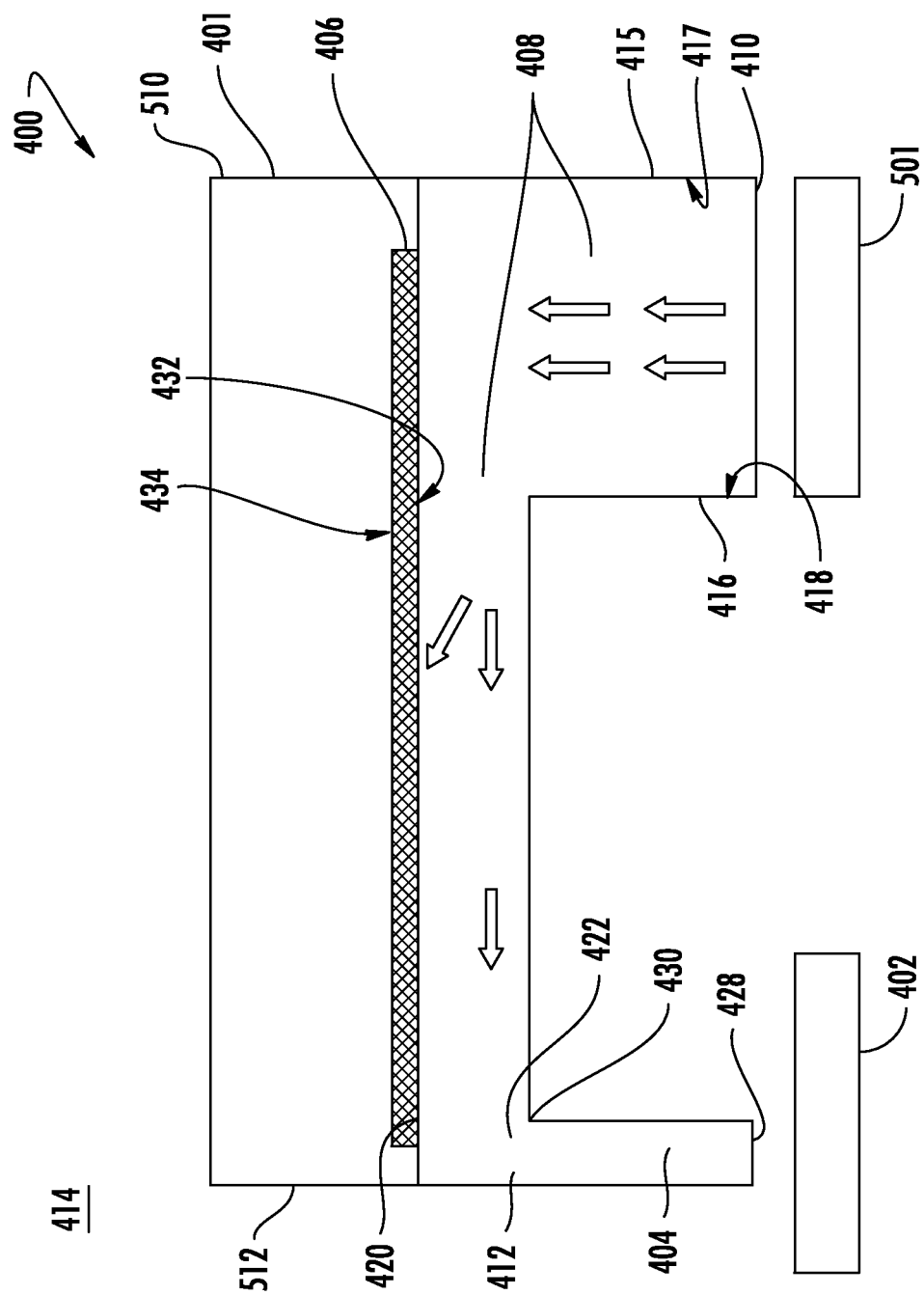
FIG. 5 provides a cross section of an example gas sensor in accordance with some embodiments discussed herein.

For instance, FIG. 5 illustrates an exemplary gas sensor 400 in accordance with some embodiments disclosed herein. In the embodiment illustrated in FIG. 5, the gas sensor 400 may include a first end 510 and a second end 512 where the inlet 410 of the test gas diffusion path 408 may be disposed at the first end of the gas sensor 400 and the sensing electrode 402 may be disposed at the second end of the gas sensor 400. The membrane 406 and capillary 404 may be disposed between the first end 510 and the second end 512 of the gas sensor 400 (that is, disposed between the sensing electrode 402 and the inlet 410 of the test gas diffusion path 408. Various configurations of the gas sensor 400 and its components may be available without deviating from the intent of the present disclosure.

Figure 6:
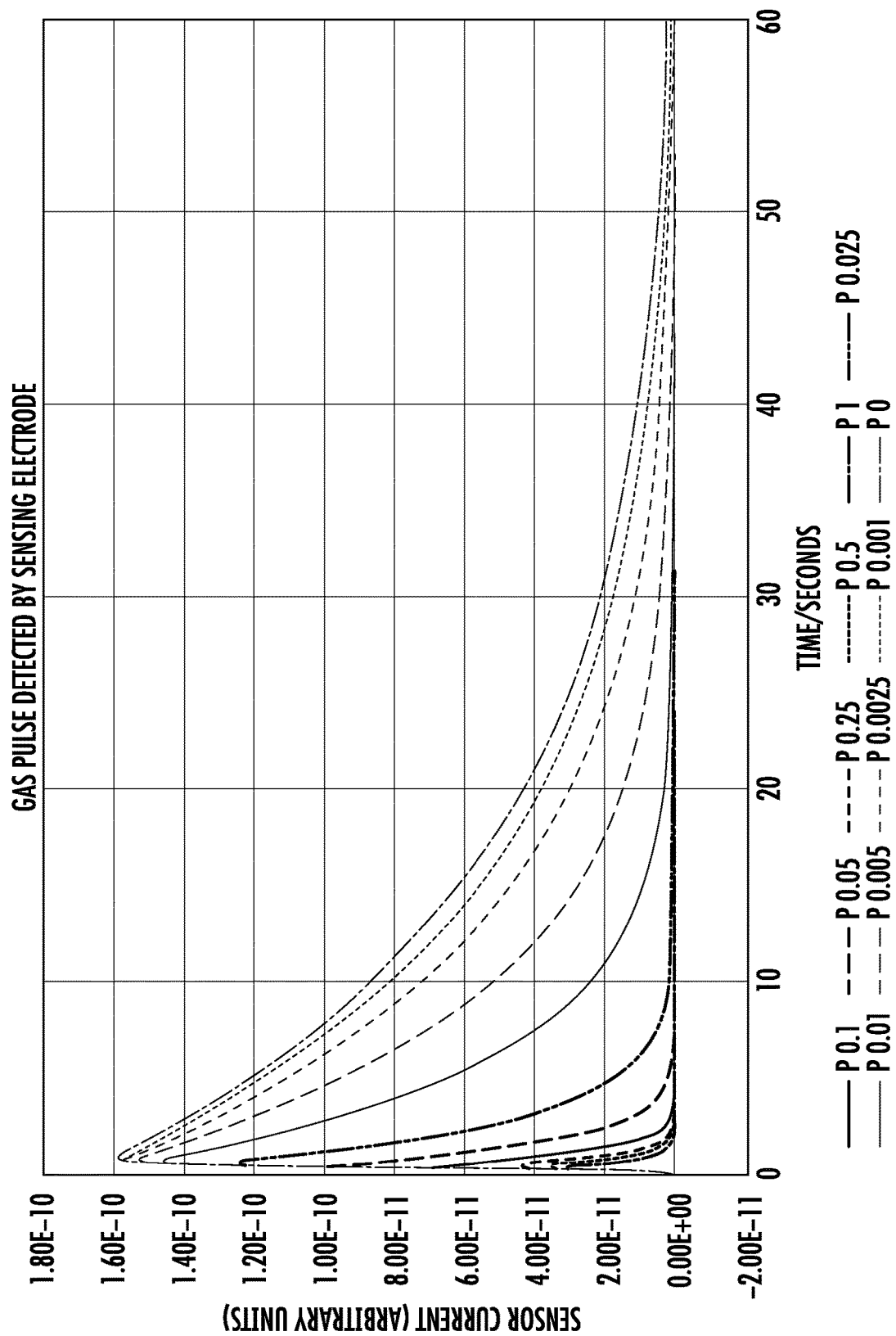
FIG. 6 provides simulation results for test gas signals detected by sensing electrodes in accordance with some embodiments discussed herein.

FIG. 6 illustrates simulation results for a diagnostic mode of a gas sensor in accordance with some embodiments disclosed herein. In particular, FIG. 6 illustrates simulation results for a test gas signal detected on the sensing electrode 402 following gas pulse generation for a range of membrane 406 porosities. The porosity is represented by "p" where a porosity of 1 is equivalent to the membrane 406 effectively not being present (e.g., the membrane is missing) and thus, the test gas escapes through the opening 420. The membrane 406 has the same diffusion coefficient as air. A porosity of zero is equivalent to a completely blocked membrane 406 such that all of the test gas flows to the sensing electrode 402.

Figure 7:
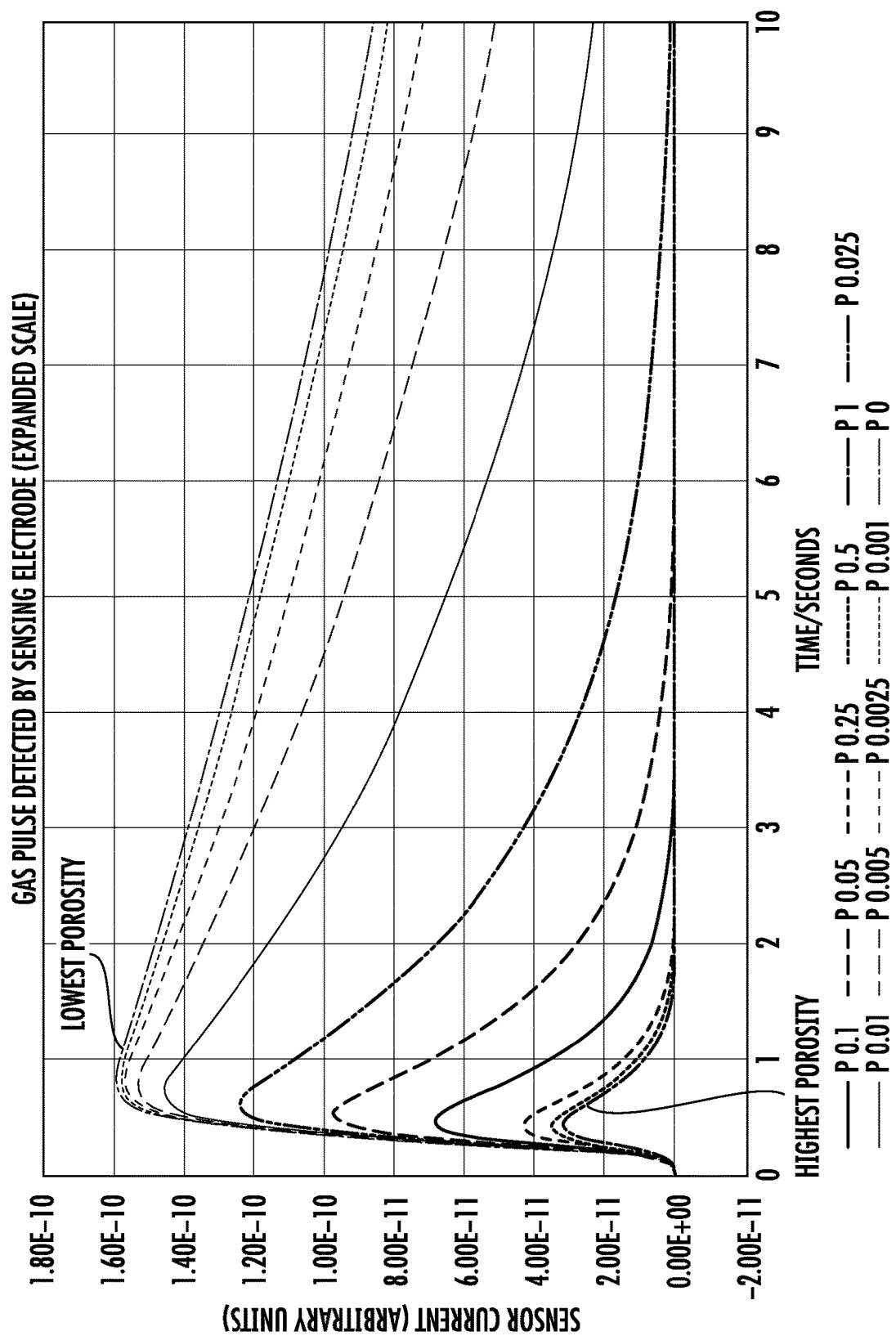
FIG. 7 provides an expanded scale of the simulation results for test gas signals detected by sensing electrodes shown in FIG. 6 in accordance with some embodiments discussed herein.

FIG. 7 illustrates an expanded scale version of the simulation results shown in FIG. 6. As shown in FIG. 7 (and FIG. 6), when the membrane 406 has a high porosity (e.g., p is 1, 0.5, or 0.25), the sensing electrode 402 produces a test gas signal that is relatively small and decays rapidly compared to the test gas signal produced when the membrane has the lowest porosity (e.g., p is zero, 0.001, or 0.0025). Most of the test gas is lost to the external environment 414 through the membrane 406 when the porosity is high. When the membrane 406 has a low porosity (e.g., p is zero, 0.001, or 0.0025), the sensing electrode 402 produces a test gas signal that is larger and has a longer decay compared to the test gas signal produced when the when the membrane has the highest porosity (e.g., p is 1, 0.5, or 0.25). Most of the test gas travels to the sensing electrode when the membrane 406 has a low porosity.

Figure 8:
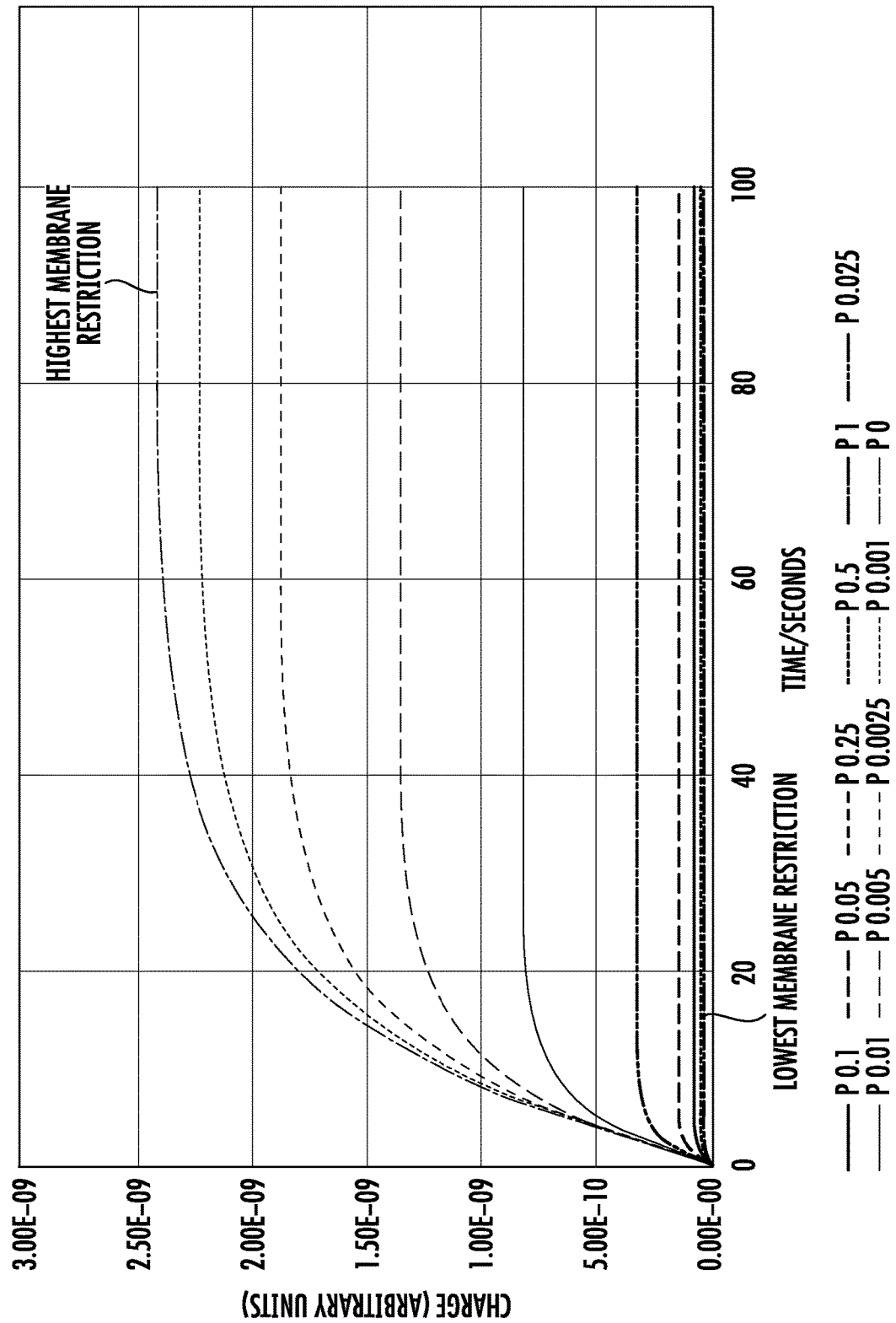
FIG. 8 provides the integrated charge on sensing electrodes for simulation results in accordance with some embodiments discussed herein.

FIG. 8 illustrates simulation results for a diagnostic mode of a gas sensor in accordance with some embodiments disclosed herein. FIG. 8 illustrates simulation results for a test gas signal detected on the sensing electrode 402 following gas pulse generation for a range of membrane 406 porosities. Again, the porosity is represented by "p" where a porosity of 1 is equivalent to the membrane 406 effectively not being present and the porosity of zero equivalent to the membrane 406 being completely blocked.

In particular, FIG. 8 illustrates the integrated charge detected by the sensing electrode 402 for various porosities. The test gas is a pulse of known charge. Thus, if no test gas is lost through the membrane 406 (e.g., the membrane 406 is completely blocked), then 100% of the test gas should be detected on the sensing electrode 402 when the charge is integrated. If all of the test gas is lost through the membrane 406, then the sensing electrode 402 detects no test gas. The integrated charge decreases as the membrane 406 is less restrictive (e.g., higher porosity).

Figure 9:
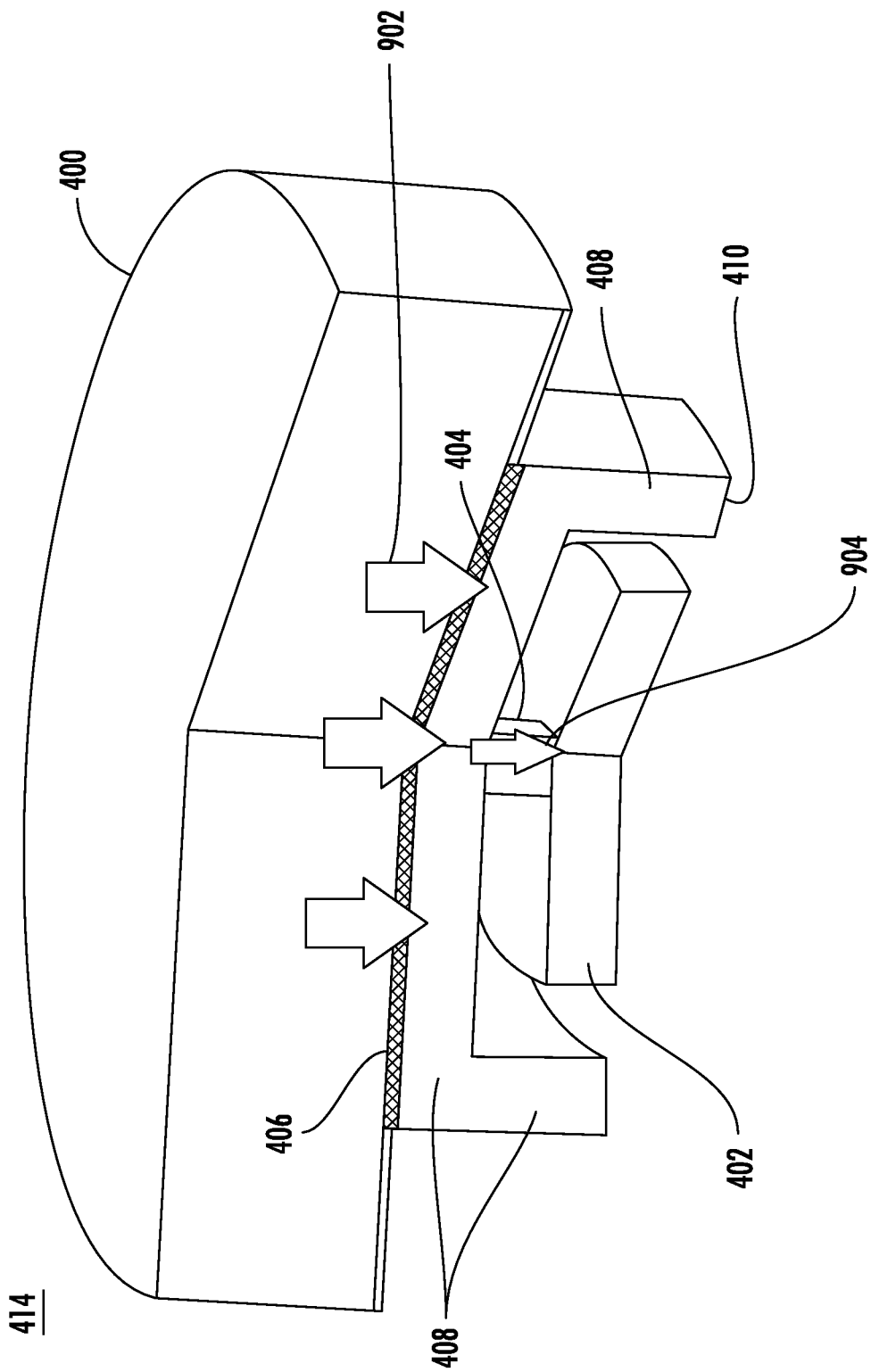
FIG. 9 provides a cross section of an example gas sensor in accordance with some embodiments discussed herein FIG. 10 provides simulation results during a normal operating mode in accordance with some embodiments discussed herein.

FIG. 9 illustrates a gas sensor during a normal operating mode in accordance with embodiments disclosed herein. In particular, during normal operating mode, air 902 travels from the external environment 414 through the membrane 406 into the gas sensor 400. The air 904 then travels through the capillary 404 to the sensing electrode 402 where the sensing electrode 402 detects the presence of target gas. As explained above, in some embodiments, test gas may be generated in the gas sensor 400. During normal operating modes, the test gas generation may be disabled such that test gas may not interfere with the sensing electrode 402 detecting target gas from the external environment 414. In some embodiments, test gas may be applied from external sources to the gas sensor 400. During normal operating modes, the test gas may be prevented from traveling through the test gas diffusion path 408 such that test gas may not interfere with the sensing electrode 402 detecting target gas from the external environment 414. Such prevention may occur by disabling a connection to the external source, physically blocking the test gas diffusion path 408, or other methods of preventing test gas from traveling through the test gas diffusion path 408.

In some embodiments, once target gas is detected by the sensing electrode 402, the gas sensor 400 may be switched from diagnostic mode to normal operating mode. For instance, while a gas sensor 400 is under diagnostic mode (e.g., causing test gas to travel through the test gas diffusion path 408), once the sensing electrode 402 detects target gas (e.g., carbon monoxide), circuitry 200 may disable the diagnostic mode (e.g., disable the test gas from traveling through the test gas diffusion path 408) so that the gas sensor 400 can be operated in the normal operating mode allowing for detection of the target gas. As the pulse of test gas that is used during the diagnostic mode is relatively small and short, switching from diagnostic mode to normal operating mode is generally quick and the gas sensor 400 can recover to normal operating mode within a short amount of time (e.g., seconds or less). For instance, test gas pulses can be 0.1 second long such that the gas sensor 400 can recover to normal operating mode in less than a second.

In some embodiments, when the target gas is detected by the sensing electrode 402 or when the gas sensor 400 is already operating in the normal operating mode, the test gas electrode 501 may be configured to detect the target gas instead of producing test gas. For instance, the test gas electrode 501 may be set to a potential where the test gas electrode 501 detects target gas and/or test gas.

Test gas pulses are generally as quick as possible and insert the smallest amount of test gas possible into the test gas diffusion path 408. The test gas pulse should be sufficient to accurately detect test gas on the sensing electrode 402 when the membrane 406 is not completely blocked and sufficient for analysis of the test gas signal generated by the sensing electrode 402. In some embodiments, the same electrolyte is used for the sensing electrode 402 as the test gas generating electrode 501. Thus, the test gas pulse should be relatively small to prevent significant reduction in the electrolyte.

Figure 10:
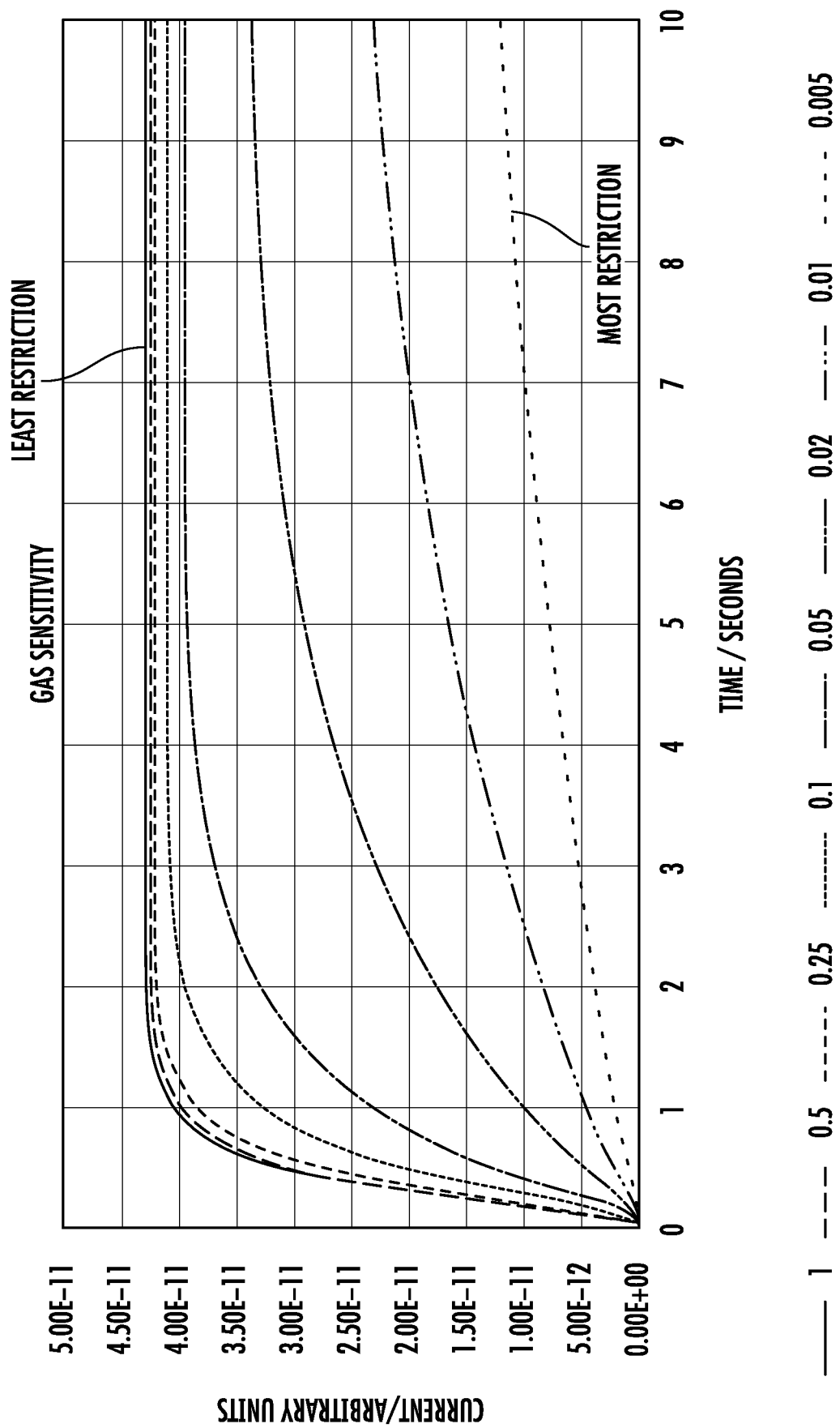

FIG. 10 illustrates simulation results of normal operating modes in accordance with some embodiments disclosed herein. In particular, FIG. 10 illustrates simulation results for target gas detected on the sensing electrode 402 for a range of membrane 406 porosities. Again, the porosity is represented by "p" where a porosity of 1 is equivalent to the membrane 406 effectively not being present and the porosity of 0.005 is equivalent to the membrane 406 being significantly blocked. As shown in FIG. 10, as the membrane 406 becomes more restricted, the response time of the gas sensor 400 slows down and the steady state signal decreases. During normal operating mode, the capillary 404 should be the most restrictive portion of the gas sensor 400. That is, the capillary 404 restricts the target gas more than the membrane 406. As the membrane 406 becomes clogged or blocked, the membrane 406 will be the more restricting section of the gas sensory 400.

Figure 11:
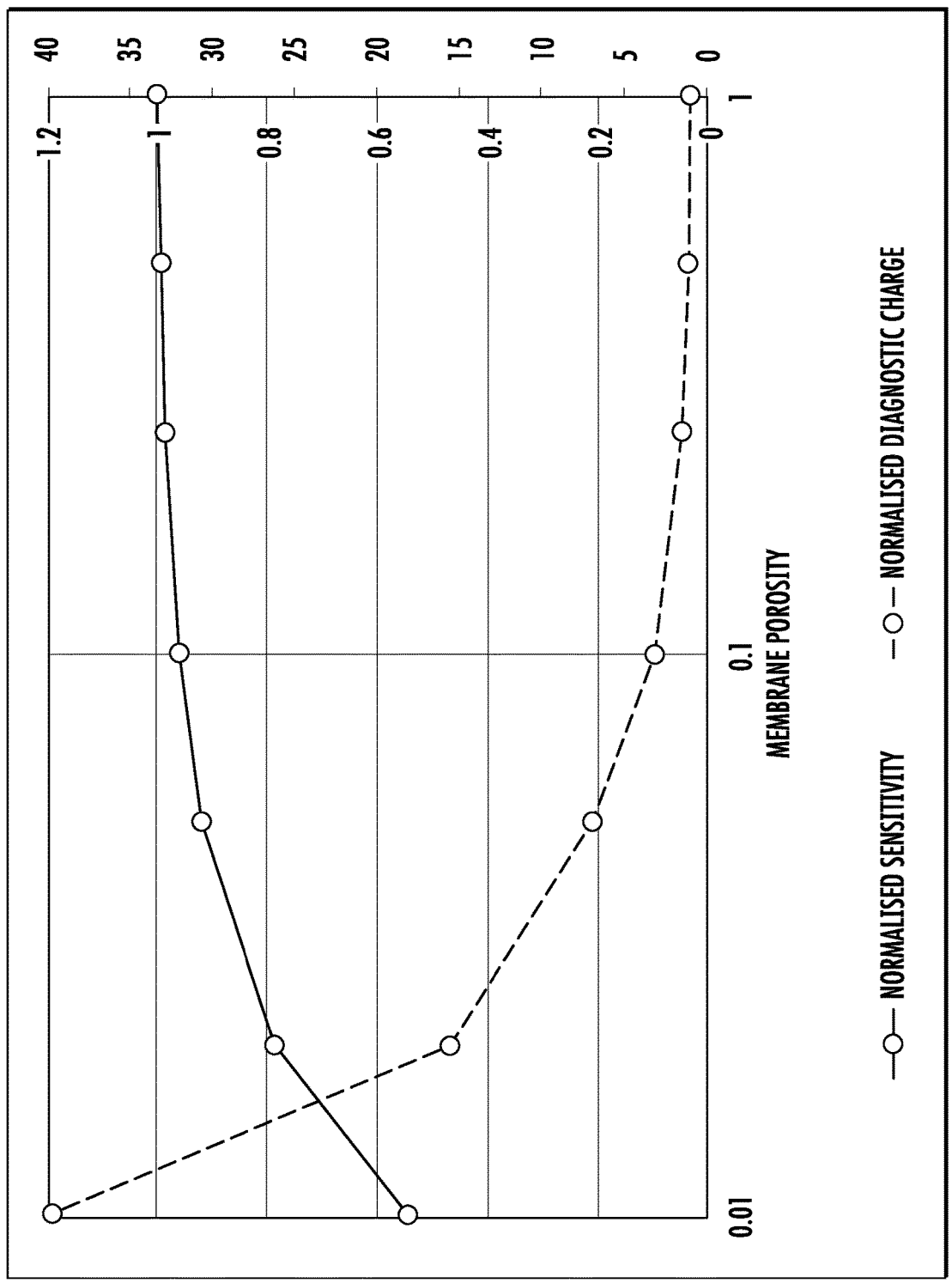
FIG. 11 illustrates the membrane porosity during a normal operating mode compared to a diagnostic mode in accordance with some embodiments discussed herein.

FIG. 11 illustrates the gas sensitivity during normal operating modes verse the gas sensitivity during the diagnostic modes. In particular, FIG. 11 compares the gas sensitivity during normal operation modes with the integrated diagnostic charge during diagnostic modes. As the membrane 406 becomes more blocked or restricted (e.g., the porosity of the membrane 406 decreases), the gas sensitivity decreases and the diagnostic charge increases. The diagnostic mode is very sensitive. For instance, when the porosity of the membrane 406 has decreased to 0.1, the gas sensitivity is still 95% of its original value and the diagnostic signal has increased three times (3×). Thus, the gas sensor 400 can provide an advanced warning of changes in the condition of the membrane 406 and capillary 404.

With the test gas diffusion path 408, the membrane 406 may be considerably restricted before the gas sensor 400 gas sensitivity is affected. The disclosed gas sensor 400 and method of using the same may be able to detect restriction of the membrane 406 long before the membrane 406 becomes restricted enough to limit gas sensitivity, thereby providing an advance warning that the gas sensor 400 needs maintenance.

The disclosed gas sensor 400 and method of using the same may enable compensation to be applied to the gas sensor 400 to allow for increased restriction by membrane 406. In extreme cases (e.g., the membrane 406 is highly restricted), failure may be flagged. The disclosed gas sensor 400 and method of using the same may also detect torn or missing membrane 406. For example, the test gas pulse reaching the sensing electrode 402 may be much lower than considered normal for the respective membrane 406. The disclosed gas sensor 400 and method of using the same may independently test (and hence compensate for and/or flag failure of) restriction of the membrane 406 and the capillary 404 using a single test. For instance, the diagnostic mode may produce a total integrated charge (e.g., the main measure for membrane 406 restriction), the peak current (e.g., the main measure for capillary 404 restriction), and the rates of rise and decay of detected test gas pulses.

The gas sensor may also include various alarms, such as visual or audible alarms, for notifying others that a gas has been identified, failure mode identified in the gas sensor, maintenance needed for the gas sensor, low power mode or loss of power, etc.

The gas sensor may include additional electrodes, chambers, membranes, capillaries, etc. arranged in various configurations without deviated from the intent of the present disclosure. The gas sensor may monitor the presence of various gases, such as carbon monoxide, and may monitor multiple gases.

Figure 12:
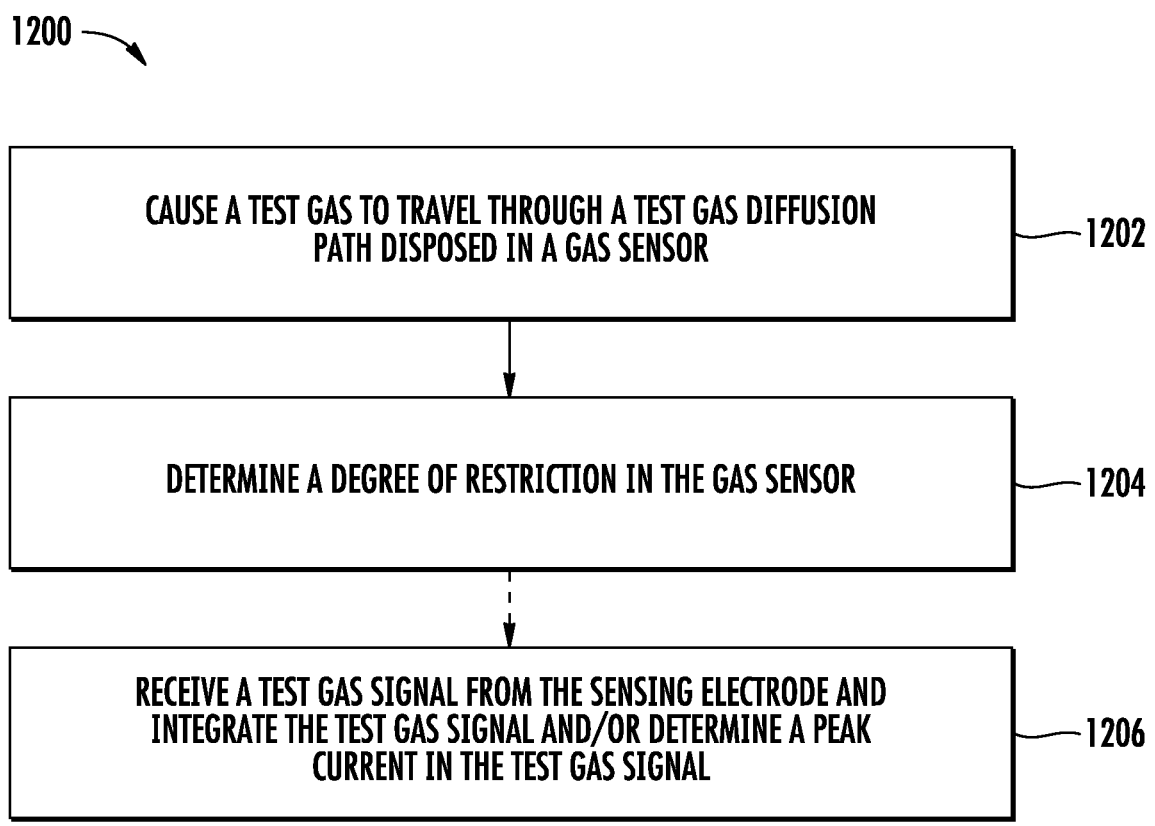
FIG. 12 provides a flowchart of example operations in accordance with some embodiments discussed herein.

FIG. 12 illustrates a flow diagram of an example system in accordance with some embodiments discussed herein. In particular, FIG. 12 illustrates a method of monitoring gas restriction in a gas sensor 400. In the embodiment illustrated in FIG. 12, the method 1200 includes causing a test gas to travel through a test gas diffusion path disposed in a gas sensor 1202 and determining a degree of restriction in the gas sensor 1204. The test gas diffusion path may be disposed between a membrane and a sensing electrode and is configured such that when the test gas travels through the test gas diffusion path from the inlet to the outlet, the test gas comes in contact with the membrane prior to coming in contact with the sensing electrode. Determining a degree of restriction in the gas sensor 1204 may include receiving a test gas signal from the sensing electrode and integrating the test gas signal and/or determining a peak current in the test gas signal 1206. For instance, the degree of restriction in the gas sensor may be determined from integrating the test gas signal, which would indicate the degree of restriction of the membrane. The degree of restriction may be determined by determining the peak current in the test gas signal, which would indicate the degree of restriction of the capillary. The method 1200 may be repeated on a periodic basis or as needed to monitor the gas sensor 400. In some embodiments, the method 1200 may include replacing and/or cleaning the membrane, capillary, or other portion of the gas sensor in response to the degree of restriction. In some embodiments, the method 1200 may include generating a restriction compensation to apply to a target gas signal in response to the degree of restriction. For instance, if the degree of restriction indicates that only a portion of the membrane and/or capillary is restricted, then a restriction compensation (e.g., a correction factor) may be applied to a target gas signal to account for the portion of the membrane and/or capillary being restricted. Such compensation may allow for accurate target gas sensing by the gas sensor with less maintenance and/or operator intervention.

Many modifications and other embodiments of the inventions set forth herein will come to mind to one skilled in the art to which these embodiments of the invention pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A gas sensor comprising:
   a housing defining an opening to an external environment;
   a sensing electrode disposed in the housing and configured to generate a test gas signal when the sensing electrode is in contact with a test gas;
   a membrane disposed in the housing between the sensing electrode and the opening in the housing, wherein the membrane is at least partially exposed to the external environment;
   a test gas diffusion path defined in the housing for the test gas to travel in the gas sensor and comprising an inlet and an outlet, wherein the test gas diffusion path is disposed between the membrane and the sensing electrode and is configured such that when the test gas travels through the test gas diffusion path from the inlet to the outlet, the test gas comes in contact with the membrane prior to coming in contact with the sensing electrode and such that the test gas signal is higher when the membrane has a high degree of restriction compared to the test gas signal when the membrane has a low degree of restriction; and
   wherein the gas sensor is configured to switch from a diagnostic mode to a normal operating mode when the sensing electrode detects a target gas.

2. The gas sensor according to claim 1, wherein the inlet of the test gas diffusion path is disposed distal to the sensing electrode and the outlet of the test gas diffusion path is disposed proximal to the sensing electrode.

3. The gas sensor according to claim 1, wherein the test gas diffusion path comprises a first test gas diffusion path opening adjacent to the membrane and between the inlet and the outlet of the test gas diffusion path and wherein the sensing electrode is disposed at the outlet of the test gas diffusion path.

4. The gas sensor according to claim 3, wherein the first test gas diffusion path opening is defined by a wall of the test gas diffusion path in the housing and the first test gas diffusion path opening exposes the test gas to the membrane.

5. The gas sensor according to claim 1, further comprising a test gas electrode configured to cause the test gas to be generated at the inlet of the test gas diffusion path.

6. The gas sensor according to claim 1, wherein the test gas comprises hydrogen, carbon monoxide, or combinations thereof.

7. The gas sensor according to claim 1, wherein the test gas is generated electrochemically.

8. The gas sensor according to claim 1, further comprising a capillary disposed between the sensing electrode and the outlet of the test gas diffusion path.

9. The gas sensor according to claim 8, wherein a magnitude of the test gas signal indicates a degree of restriction of the capillary.

10. The gas sensor according to claim 1, wherein the gas sensor is configured to generate the test gas at periodic intervals of time.

11. The gas sensor according to claim 1, wherein an integrated charge of the test gas signal indicates the degree of restriction of the membrane.

12. The gas sensor according to claim 1, wherein the gas sensor is configured to cause test gas to enter the inlet of the test gas diffusion path during the diagnostic mode and to cause test gas to be restricted from entering the inlet of the test gas diffusion path during the normal operating mode.

13. The gas sensor according to claim 1, wherein the gas sensor is configured to switch from the diagnostic mode to the normal operating mode in less than one second.

14. The gas sensor according to claim 1, wherein the inlet of the test gas diffusion path is disposed concentrically around the sensing electrode.

15. The gas sensor according to claim 1, wherein the inlet of the test gas diffusion path is disposed at a first end of the housing and the sensing electrode is disposed at a second end of the housing.

16. The gas sensor according to claim 1, wherein the test gas is generated by an external test gas generator, and wherein when the external test gas generator generates the test gas, the gas sensor and the external test gas generator are operatively coupled such that the test gas enters the inlet of the test gas diffusion path of the gas sensor.

17. A method of monitoring gas restriction in a gas sensor, the method comprising:
  causing a test gas to travel through a test gas diffusion path disposed in the gas sensor and comprising an inlet and an outlet, wherein the test gas diffusion path is disposed between a membrane and a sensing electrode and is configured such that when the test gas travels through the test gas diffusion path from the inlet to the outlet, the test gas comes in contact with the membrane prior to coming in contact with the sensing electrode;
  determining a degree of restriction in the gas sensor, and
  wherein determining the degree of restriction in the gas sensor comprise receiving a test gas signal from the sensing electrode and integrating the test gas signal.

18. The method according to claim 17, wherein the degree of restriction is associated with the membrane.

19. The method according to claim 17, wherein determining the degree of restriction in the gas sensor further comprises determining a peak current in the test gas signal and wherein the degree of restriction is associated with a capillary disposed between the membrane and the sensing electrode.

20. The method according to claim 17, further comprising applying a restriction compensation to the target gas signal in response to determining the degree of restriction.

* * * * *